(12) United States Patent
Chatterjee et al.

(10) Patent No.: US 12,049,639 B2
(45) Date of Patent: *Jul. 30, 2024

(54) CANCER IMMUNOTHERAPY BY DELIVERING CLASS II MHC ANTIGENS USING A VLP-REPLICON

(71) Applicant: The USA as represented by the Secretary, Department of Health and Human Services, Bethesda, MD (US)

(72) Inventors: Deb K. Chatterjee, Potomac, MD (US); Stanislaw J. Kaczmarczyk, Frederick, MD (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/174,013

(22) Filed: Feb. 24, 2023

(65) Prior Publication Data

US 2023/0257775 A1 Aug. 17, 2023

Related U.S. Application Data

(62) Division of application No. 17/120,497, filed on Dec. 14, 2020, now Pat. No. 11,718,861, which is a division of application No. 15/104,785, filed as application No. PCT/US2014/070552 on Dec. 16, 2014, now abandoned.

(60) Provisional application No. 61/916,394, filed on Dec. 16, 2013.

(51) Int. Cl.
| | |
|---|---|
| *C12N 15/86* | (2006.01) |
| *A61K 39/00* | (2006.01) |
| *A61K 39/12* | (2006.01) |
| *A61K 45/06* | (2006.01) |
| *C12N 7/00* | (2006.01) |

(52) U.S. Cl.
CPC ......... *C12N 15/86* (2013.01); *A61K 39/0011* (2013.01); *A61K 39/001117* (2018.08); *A61K 39/001124* (2018.08); *A61K 39/001129* (2018.08); *A61K 39/001144* (2018.08); *A61K 39/001152* (2018.08); *A61K 39/001163* (2018.08); *A61K 39/001181* (2018.08); *A61K 39/001182* (2018.08); *A61K 39/001191* (2018.08); *A61K 39/001194* (2018.08); *A61K 39/12* (2013.01); *A61K 45/06* (2013.01); *C12N 7/00* (2013.01); *A61K 2039/5258* (2013.01); *A61K 2039/53* (2013.01); *A61K 2039/585* (2013.01); *C12N 2740/11023* (2013.01); *C12N 2740/11042* (2013.01); *C12N 2770/36123* (2013.01); *C12N 2770/36134* (2013.01); *C12N 2770/36143* (2013.01); *C12N 2770/36145* (2013.01); *C12N 2770/36152* (2013.01); *C12N 2770/36171* (2013.01); *C12N 2800/24* (2013.01); *C12N 2810/6081* (2013.01)

(58) Field of Classification Search
None
See application file for complete search history.

(56) References Cited

U.S. PATENT DOCUMENTS

| | | | |
|---|---|---|---|
| 5,071,651 A | 12/1991 | Sabara et al. | |
| 5,374,426 A | 12/1994 | Sabara et al. | |
| 5,631,237 A | 5/1997 | Dzau et al. | |
| 6,099,847 A | 8/2000 | Tobin et al. | |
| 6,149,905 A | 11/2000 | Ostrand-Rosenberg et al. | |
| 6,541,010 B1 | 4/2003 | Johnston et al. | |
| 6,783,939 B2 | 8/2004 | Olmsted et al. | |
| 6,902,886 B1 | 6/2005 | Citovsky et al. | |
| 7,425,337 B2 | 9/2008 | Smith et al. | |
| 9,296,790 B2 | 3/2016 | Chatterjee et al. | |
| 9,506,041 B2 | 11/2016 | Kaczmarczyk et al. | |
| 10,040,830 B2 | 8/2018 | Chatterjee et al. | |
| 10,538,743 B2 | 1/2020 | Kaczmarczyk et al. | |
| 10,577,397 B2 | 3/2020 | Chatterjee et al. | |
| 11,718,861 B2 * | 8/2023 | Chatterjee ...... | A61K 39/001182 424/192.1 |
| 2002/0052040 A1 | 5/2002 | Hunt | |
| 2002/0177551 A1 | 11/2002 | Terman | |
| 2008/0118956 A1 | 5/2008 | Pages et al. | |
| 2011/0250675 A1 | 10/2011 | Bennet et al. | |

(Continued)

FOREIGN PATENT DOCUMENTS

| | | |
|---|---|---|
| JP | 2002-532115 | 10/2002 |
| JP | 2007-512827 | 5/2007 |

(Continued)

OTHER PUBLICATIONS

Pishesha et al. "A guide to antigen processing and presentation," Nature Reviews, Dec. 2022, vol. 22, pp. 751-764.
"CD80," Wikipedia, last edited Oct. 9, 2018, 6 pages [retrieved online Dec. 5, 2018 from: en.wikipedia.org/w/inxes.php?title=CD80&oldid=863258087].
Akkina et al., "High-efficiency gene transfer into CD34+ cells with a human immunodeficiency virus type 1-based retroviral vector pseudotyped with vesicular stomatitis virus envelope glycoprotein G.", J Virol. 1996, vol. 70(4), pp. 2581-2585.

(Continued)

*Primary Examiner* — Nancy J Leith
(74) *Attorney, Agent, or Firm* — Sheridan Ross P.C.

(57) ABSTRACT

Described herein is a method of preventing or treating a disease in a mammalian subject, comprising administering to the subject who is in need thereof an effective dosage of a pharmaceutical composition comprising a virus like particle (VLP) comprising: an alphavirus replicon comprising a recombinant polynucleotide, wherein the polynucleotide comprises a sequence encoding both subunits of a human class II major histocompatibility antigen, a retroviral gag protein, and a fusogenic envelope protein, wherein the VLP does not contain an alphavirus structural protein gene.

15 Claims, 5 Drawing Sheets
Specification includes a Sequence Listing.

(56) References Cited

U.S. PATENT DOCUMENTS

| | | |
|---|---|---|
| 2016/0312242 A1 | 10/2016 | Chatterjee et al. |
| 2020/0102545 A1 | 4/2020 | Kaczmarczyk et al. |
| 2021/0163988 A1 | 6/2021 | Chatterjee et al. |

FOREIGN PATENT DOCUMENTS

| | | |
|---|---|---|
| JP | 2012-140447 | 7/2012 |
| JP | 2012-143245 | 8/2012 |
| JP | 2012-524780 | 10/2012 |
| WO | WO 92/11291 | 7/1992 |
| WO | WO 96/30523 | 10/1996 |
| WO | WO 98/15631 | 4/1998 |
| WO | WO 01/44481 | 6/2001 |
| WO | WO 02/080982 | 10/2002 |
| WO | WO 03/024481 | 3/2003 |
| WO | WO 2005/042695 | 5/2005 |
| WO | WO 2005/115444 | 12/2005 |
| WO | WO 2006/059141 | 6/2006 |
| WO | WO 2007/130330 | 11/2007 |
| WO | WO 2008/115199 | 9/2008 |
| WO | WO 2011/056899 | 5/2011 |
| WO | WO 2013/148302 | 10/2013 |

OTHER PUBLICATIONS

Alefantis et al., "Characterization of a Nuclear Export Signal within the Human T Cell Leukemia Virus Type I Transactivator Protein Tax," The Journal of Biological Chemistry, 2003, vol. 278(24), pp. 21814-21822.

Altschul et al., "Basic Local Alignment Search Tool," Journal of Molecular Biology, 1990, vol. 215, pp. 403-410.

Altschul et al., "Gapped BLAST and PSI-BLAST: a new generation of protein database search programs," Nucleic Acids Research, 1997, vol. 25(17), pp. 3389-3402.

Anderson "Tumor Vaccines for Breast Cancer," Cancer Invest., May 2009, vol. 27, No. 4, pp. 361-368.

Armstrong et al. "Major histocompatibility complex calss II-transsfected tumor cells present endogenous antigen and are potent inducers of tumor-specific immunity," Proceedings of the National Academy of Sciences, Jun. 1997, vol. 94, No. 13, pp. 6886-6891, Jun. 16, 2023.

Bogerd et al., Protein Sequence Requirements for Function of the Human T-Cell Leukemia Virus Type 1 Rex Nuclear Export Signal Delineated by a Novel In Vivo Randomization-Selection Assay, Molecular and Cellular Biology, 1996, vol. 16(8), pp. 4207-4214.

Bredenbeek et al. "Sindbis Virus Expression Vectors: Packaging of RNA Replicons by Using Defective Helper RNAs," Journal of Virology, Nov. 1993, vol. 67, No. 11, pp. 6439-6446.

Briggs, "The stoichiometry of Gag protein in HIV-1," Nature Structural & Molecular Biology, 2004, vol. 11(7), pp. 672-675.

Carriere et al., "Sequence Requirements for Encapsidation of Deletion Mutants and Chimeras of Human Immunodeficiency Virus Type 1 Gag Precursor into Retrovirus-Like Particles," Journal of Virology, 1995, vol. 69(4), pp. 2366-2377.

Chauhan et al., "The taming of the cell penetrating domain of the HIV Tat: Myths and realities," Journal of Controlled Release, 2007, vol. 117, pp. 148-162.

Chazal et al., "Virus Entry, Assembly, Budding, and Membrane Rafts," Microbiology and Molecular Biology Reviews, 2003, vol. 67(2), pp. 226-237.

Coskun-Ari et al., "Sequence-specific Interactions in the Tus-Ter Complex and the Effect of Base Pair Substitutions on Arrest of DNA Replication in *Escherichia coli*" The Journal of Biological Chemistry, 1997, vol. 272(42), pp. 26448-26456.

Cyert, "Regulation of Nuclear Localization during Signaling," The Journal of Biological Chemistry, 2001, vol. 276(24), pp. 20805-20808.

Deml et al. "Recombinant HIV-1 Pr55gag virus-like particles: potent stimulators of innate and acquired immune responses," Molecular Immunology, 2005, vol. 42(2), pp. 259-277.

Deo et al. "Expression of an RSV-gag virus-like particle in insect cell lines and silkworm larvae," Journal of Virological Methods, 2011, vol. 177, pp. 147-152.

Diatta et al. "Semliki Forest virus-derived virus-like particles: characterization of their production and transduction pathways," Journal of General Virology, Nov. 2005, vol. 86, pp. 3129-3136.

Dunn et al. "Retroviral proteases," Genome Biology, 2002, vol. 3(4), pp. 3006.1-3006.7.

Dworetzky et al., "Translocation of RNA-Coated Gold Particles Through the Nuclear Pores of Oocytes," The Journal of Cell Biology, 1988, vol. 106, pp. 575-584.

Facke et al., "A Large Deletion in the Matrix Domain of the Human Immunodeficiency Virus gag Gene Redirects Virus Particle Assembly from the Plasma Membrane to the Endoplasmic Reticulum," Journal of Virology, 1993, vol. 67(8), pp. 4972-4980.

Fischer et al., "The HIV-1 Rev Activation Domain Is a Nuclear Export Signal That Accesses an Export Pathway Used by Specific Cellular RNAs," Cell, 1995, vol. 82, pp. 475-483.

Fornerod et al., "CRM1 Is an Export Receptor for Leucine-Rich Nuclear Export Signals," Cell, 1997, vol. 90, pp. 1051-1060.

Freed "HIV-1 Gag Proteins: Diverse Functions in the Virus Life Cycle," Virology, 1998, vol. 251, Article No. VY989398, 15 pages.

Frolov et al. "Selection of RNA Replicons Capable of Persistent Noncytopathic Replication in Mammalian Cells," Journal of Virology, May 1999, vol. 73, No. 5, pp. 3854-3865.

Frolov et al. "Alphavirus-based expression vectors: Strategies and applications," PNAS, Oct. 1996, vol. 93, pp. 11371-11377.

Gangeten et al., "Brief expression of a GFPcre fusion gene in embryonic stem cells allows rapid retrieval of site-specific genomic deletions," Nucleic Acids Research, 1997, vol. 25(16), pp. 3326-3331.

Gerace, "Nuclear Export Signals and the Fast Track to the Cytoplasm," Cell, 1995, vol. 82, pp. 341-344.

Gonzalez-Navajas et al. "Immunomodulatory functions of type 1 interferons," Nature Review Immunology, col. 12, 2012, pp. 125-135.

Gorlich et al., "Nucleocytoplasmic Transport," Science, 1996, vol. 271, pp. 1513-1518.

Gottlieb et al., "Equilibrium, Kinetic, and Footprinting Studies of the Tus-Ter Protein-DNA Interaction," The Journal of Biological Chemistry, 1992, vol. 267(11), pp. 7434-7443.

Gottlinger et al., "Role of capsid precursor processing and myristoylation in morphogenesis and infectivity of human immunodeficiency virus type 1," PNAS, 1989, vol. 86(15), pp. 5781-5785.

Guibinga et al. "Baculovirus GP64-Pseudotyped HIV-Based Lentivirus Vectors are Stabilized Against Complement Inactivation by Codisplay of Decay Accelerating Factor (DAF) or of a GP64-DAF Fusion Protein," Molecular Therapy, 2005, vol. 11(4), pp. 645-651.

Haglund et al. "Expression of Human Immunodeficiency Virus Type 1 Gag Protein Precursor and Envelope Proteins from a Vesicular Stomatitis Virus Recombinant: High-Level Production of Virus-like Particles Containing HIV Envelope," Virology, 2000, vol. 268, pp. 112-121.

Hajek et al. "Proteolytic Processing and Assembly of gag and gag-pol Proteins of TED, a Baculovirus-Associated Retrotransposon of the Gypsy Family," Journal of Virology, 1998, vol. 72(11), pp. 8718-8724.

Harvey et al. "Kunjin Virus Replicon Vectors for Human Immunodeficiency Virus Vaccine Development," Journal of Virology, Jul. 2003, vol. 77, No. 14, pp. 7796-7803.

Harvey et al. Tetracycline-Inducible Packaging Cell Line for Production of Flavivirus Replicon Particles, Journal of Virology, 2004, vol. 78(1), pp. 531-538.

Hong et al., "Assembly-Defective Point Mutants of the Human Immunodeficiency Virus Type 1 Gag Precursor Phenotypically Expressed in Recombinant Baculovirus-Infected Cells," Journal of Virology, 1993, vol. 67(5), pp. 2787-2798.

Ikuta et al., "Nuclear Localization and Export Signals of the Human Aryl Hydrocarbon Receptor," The Journal of Biological Chemistry, 1998, vol. 273(5), pp. 2895-2904.

Jans et al., "Nuclear targeting signal recognition: a key control point in nuclear transport?," BioEssays 22.6, pp. 532-544, 2000.

(56) References Cited

OTHER PUBLICATIONS

Jiang et al., "Norwalk Virus Genome Cloning and Characterization," Science, 1990, vol. 250, pp. 1580-1583.
Jurgens et al. "A Novel Self-Replicating Chimeric Lentivirus-Like Particle," Journal of Virology, Jan. 2012, vol. 86, No. 1, pp. 246-261.
Kaczmarczyk et al. "Protein delivery using engineered virus-like particles," Proceedings of the National Academy of Science USA, Oct. 2011, vol. 108, No. 41, pp. 16998-17003.
Kalderon et al., "A Short Amino Acid Sequence Able to Specify Nuclear Location," Cell, 1984, vol. 39, pp. 499-509.
Kamada et al., "Structure of a replication-terminator protein complexed with DNA," Nature, 1996, vol. 383, pp. 598-603.
Karliin et al., "Methods for assessing the statistical significance of molecular sequence features by using general scoring schemes," PNAS, 1990, vol. 87, pp. 2264-2268.
Karlin et al., "Applications and statistics for multiple high-scoring segments in molecular sequences," PNAS, 1993, vol. 90, pp. 5873-5877.
Kent et al. "Evaluation of recombinant Kunjin replicon SIV vaccines for protective efficacy in macaques," Virology, 2008, vol. 374(2), pp. 528-534.
Kuempel et al., "Bidirectional Termination of Chromosome Replication in *Escherichia coli*," Mol. Gen. Genet., 1973, vol. 125, pp. 1-8.
Kurisaki et al., "The Mechanism of Nuclear Export of Smad3 Involves Exportin 4 and Ran," Molecular and Cellular Biology, 2006, vol. 26(4), pp. 1318-1332.
Le et al., "Nuclear targeting determinants of the phage P1 Cre DNA recombinase," Nucleic Acids Research, 1999, vol. 27(24), pp. 4703-4709.
Leb et al. "Modulation of allergen-specific T-lymphocyte function by virus-like particles decorated with HLA class II molecules," Journal of Allergy and Clinical Immunology, Jul. 2009, vol. 124, No. 1, pp. 121-128.
Lewis et al. "Development of an Avian Leukosis-Sarcoma Virus Subgroup A Pseudotyped Lentiviral Vector," Journal of Virology, 2001, vol. 75(19), pp. 9339-9344.
Li et al. "Production of infectious recombinant Moloney murine leukemia virus particles in BHK cells using Semliki Forest virus-derived RNA expression vectors," Proceedings of the National Academy of Science USA, Oct. 1996, vol. 93, pp. 11658-11663.
Lin et al. "Treatment of Established Tumors with a Novel Vaccine That Enhances Major Histocompatibility Class II Presentation of Tumor Antigen," Cancer Research, Jan. 1996, vol. 56, No. 1, pp. 21-26.
Link et al., "Therapeutic protein transduction of mammalian cells and mice by nucleic acid-free lentiviral nanoparticles," Nucleic Acids Research, 2006, vol. 34(2), e16, pp. 1-10.
Luo et al. "Chimeric gag-V3 virus-like particles of human immunodeficiency virus induce virus-neutralizing antibodies," PNAS, Nov. 1992, vol. 89, No. 21, pp. 10527-10531.
Luo et al. "Induction of V3-Specific Cytotoxic T Lymphocyte Responses by HIV gag Particles Carrying Multiple Immunodominant V3 Epitopes of gp 120," Virology, 1998, vol. 240, pp. 316-325.
Masters et al., "Evidence for the Bidirectional Replication of the *Escherichia coli* Chromosome," Nature New Biology, 1971, vol. 232, pp. 137-140.
Matsui et al., "The Isolation and Characterization of a Norwalk Virus-specific cDNA," Journal of Clinical Investigation, 1991, vol. 87, pp. 1456-1461.
Mazarakis et al. "Rabies virus glycoprotein pseudotyping of lentiviral vectors enables retrograde axonal transport and access to the nervous system after peripheral delivery," Human Molecular Genetics, 2001, vol. 10(19), pp. 2109-2121.
Mervis et al. "The gag gene products of human immunodeficiency virus type 1: alignment within the gag open reading frame, identification of posttranslational modifications, and evidence for alternative gag precursors." Journal of Virology, 1988, vol. 62(11), pp. 3993-4002.
Michel et al. "Optimisation of secretion of recombinant HBsAg virus-like particles: Impact on the development of HIV-1/HBV bivalent vaccines," Vaccine, 2007, 2006, vol. 25, pp. 1901-1911.
Moll et al., "Designed heterodimerizing leucine zippers with a range of pIs and stabilities up to 10-15 M," Protein Science, 2001, vol. 10, pp. 649-655.
Morling et al. "Masking of Retroviral Envelope Functions by Oligomerizing Polypeptide Adaptors," Virology, 1997, vol. 234, pp. 51-61.
Mulugu et al., "Mechanism of termination of DNA replication of *Escherichia coli* involves helicase-contrahelicase interaction," PNAS, 2001, vol. 98(17), pp. 9569-9574.
Murriel et al., "Influence of protein transduction domains on intracellular delivery of macromolecules," Expert Opinion on Drug Delivery, 2006, vol. 3(6), pp. 739-746.
Naldini et al. "Efficient transfer, integration, and sustained long-term expression of the transgene in adult rat brains injected with a lentiviral vector," PNAS, 1996, vol. 93, pp. 11382-11388.
Naldini et al. "In Vivo Gene Delivery and Stable Transduction of Nondividing Cells by a Lentiviral Vector," Science, 1996, vol. 272, pp. 263-267.
Newmeyer et al., "Nuclear Import Can Be Separated into Distinct Steps In Vitro: Nuclear Pore Binding and Translocation," Cell, 1988, vol. 52, pp. 641-653.
Neylon et al., "Interaction of the *Escherichia coli* Replication Terminator Protein (Tus) with DNA: A Model Derived from DNA-Binding Studies of Mutant Proteins by Surface Plasmon Resonance," Biochemistry, 2000, vol. 39, pp. 11989-11999.
Neylon et al., Replication Termination in *Escherichia coli*: Structure and Antihelicase Activity of the Tus-Ter Complex, Microbiology and Molecular Biology Reviews, 2005, vol. 69(3), pp. 501-526.
Okimoto et al. "VSV-G Envelope Glycoprotein Forms Complexes with Plasmid DNA and MLV Retrovirus-like Particles in Cell-free Conditions and Enhances DNA Transfection," Molecular Therapy, Sep. 2001, vol. 4, No. 3, pp. 232-238.
Owais et al., "Liposome-mediated cytosolic delivery of macromolecules and its possible use in vaccine development, " European Journal of Biochemistry, 2000, vol. 267, pp. 3946-3956.
Patel et al., "Natively Unfolded Nucleoporins Gate Protein Diffusion across the Nuclear Pore Complex," Cell, 2007, vol. 129, pp. 83-96.
Peitz et al., "Ability of the hydrophobic FGF and basic TAT peptides to promote cellular uptake of recombinant Cre recombinase: A tool for efficient genetic engineering of mammalian genomes," PNAS, 2002, vol. 99(7), pp. 4489-4494.
Pelczar et al., "Agrobacterium proteins VirD2 and VirE2 mediate precise integration of synthetic T-DNA complexes in mammalian cells," European Molecular Biology Organization, 2004, vol. 5(6), pp. 632-637.
Peretti et al: "Cell Death Induced by the Herpes Simplex Virus-1 Thymidine Kinase Delivered by Human Immunodeficiency Virus-1-Based Virus-like Particles", Molecular Therapy7, Academic Press, 2005, vol. 12(6), pp. 1185-1196.
Perez et al. "The Transmembrane Glycoprotein of Human Immunodeficiency Virus Type 1 Induces Syncytium Formation in the Absence of the Receptor Binding Glycoprotein," Journal of Virology, 1992, vol. 66(7), pp. 4134-4143.
Perri et al. "Replicon Vectors Derived from Sindbis Virus and Semliki Forest Virus That Establish Persistent Replication in Host Cells," Journal of Virology, Oct. 2000, vol. 74, No. 20, pp. 9802-9807.
Piver et al. "Mobilization of Full-Length Semliki Forest Virus Replicon by Retrovirus Particles," Journal of Virology, Oct. 2006, vol. 80, No. 19, pp. 9889-9895.
Pulaski et al. "Immunotherapy with vaccines combining MHC class II/CD80+ tumor cells with interleukin-12 reduces established metastatic disease and stimulates immune effectors and monokine induced by interferon y," Cancer Immunology and Immunotherapy, Jan. 2000, vol. 49, No. 1, pp. 34-45.
Pulaski et al. "Reduction of Established Spontaneous Mammary Carcinoma Metastases following Immunotherapy with Major His-

(56) References Cited

OTHER PUBLICATIONS tocompatibility Complex Class II and B7.1 Cell-based Tumor Vaccines," Cancer Research, Jan. 1998, vol. 58, No. 7, pp. 1486-1493.
Pulaski et al. "Cooperativity of *Staphylococcal aureus* Enterotoxin B Superantigen, Major Histocompatibility Complex Class II, and CD80 for Immunotherapy of Advanced Spontaneous Metastases in a Clinically Relevant Postoperative Mouse Breast Cancer model," Cancer Research, May 2000, vol. 60, No. 10, pp. 2710-2715.
Reiser et al. "Induction of B7-1 in podocytes is associated with nephrotic syndrome," Journal of Clinical Investigation, May 2004, vol. 113, No. 10, pp. 1390-1397.
Richardson et al., "Nuclear Protein Migration Involves Two Steps: Rapid Binding at the Nuclear Envelope Followed by Slower Translocation through Nuclear Pores," Cell, 1988, vol. 52, pp. 655-664.
Robbins et al., "Two Interdependent Basic Domains in Nucleoplasmin Nuclear Targeting Sequence: Identification of a Class of Bipartite Nuclear Targeting Sequence," Cell, 1991, vol. 64, pp. 615-623.
Royer et al., "Expression and Extracellular Release of Human Immunodeficiency Virus Type 1 Gag Precursors by Recombinant Baculovirus-Infected Cells," Journal of Virology, 1992, vol. 66(5), pp. 3230-3235.
Saito et al. Oncolytic virotherapy for oral squamous cell carcinoma using replication-competent viruses, Oral Oncology, 2009, vol. 45, pp. 1021-1027.
Sasnauskas et al., "Generation of Recombinant Virus-Like Particles of Human and Non-Human Polyomaviruses in Yeast *Saccharomyces cerevisiae*," Intervirology, 2002, vol. 45, pp. 308-317.
Sasnauskas et al., "Yeast Cells Allow High-Level Expression and Formation of Polyomavirus-Like Particles," Biological Chemistry, 1999, vol. 380, pp. 381-386.
Schell et al. "Significant Protection against High-Dose Simian Immunodeficiency Virus Challenge Conferred by a New Prime-Boos Vaccine Regimen," Journal of Virology, Jun. 2011, vol. 85, No. 12, pp. 5764-5772.
Schwarze et al., "Protein transduction: unrestricted delivery into all cells?," Cell Biology, 2000, vol. 10, pp. 290-295.
Siegel et al. "Sequence-specific recognition of a subgenomic RNA promoter by a viral RNA polymerase," PNAS, Oct. 1997, vol. 94, pp. 11238-11243.
Skokotas et al., "Mutations in the *Escherichia coli* Tus Protein Define a Domain Positioned Close to the DNA in the Tus-Ter Complex," The Journal of Biological Chemistry, 1995, vol. 270(52), pp. 30941-30948.
Smerdou et al. "Non-viral amplification systems for gene transfer: Vectors based on alphaviruses," Current Opinion in Molecular Therapeutics, 1999, vol. 1, No. 2, pp. 244-251.
Smit et al. "Flavivirus Cell Entry and Membrane Fusion," Virus, 2011, vol. 3, pp. 160-171.
Spearman et al., "Identification of Human Immunodeficiency Virus Type 1 Gag Protein Domains Essential to Membrane Binding and Particle Assembly," Journal of Virology, 1994, vol. 68(5), pp. 3232-3242.
Srivastava et al. "Lung cancer patients' CD4+ T cells are activated in vitro by MHC Il cell-based vaccines despite the presence of Myeloid-derived suppressor cells," Cancer Immunology, Immunotherapy, Mar. 2008, vol. 57, No. 10, pp. 1493-1504.
Tsuji et al. "Production of Rous sarcoma virus-like particles displaying human transmembrane protein in silkworm larvae and its application to ligand-receptor binding assay," Journal of Biotechnology, 2011, vol. 155, pp. 185-192.
Twomey et al., "Structure and immunogenicity of experimental foot-and-mouth disease and poliomyelitis vaccines," Vaccine, 1995, vol. 13(16), pp. 1603-1610.
Ulrich et al., "Core Particles of Hepatitis B Virus as Carrier for Foreign Epitopes," Advances in Virus Research, 1998, vol. 50, pp. 141-182.
Varnavski et al. "Noncytopathic Flavivirus Replicon RNA-Based System for Expression and Delivery of Heterologous Genes," Virology 1999, vol. 255(2), pp. 366-375.
Wagner et al. "Construction, Expression, and Immunogenicity of Chimeric HIV-1 Virus-like Particles," Virology, 1996, vol. 220, pp. 128-140.
Warnes et al., "Expression of the measles virus nucleoprotein gene in *Escherichia coli* and assembly of nucleocapsid-like structures," Gene, 1995, vol. 160, pp. 173-178.
Weldon, Jr. et al. "Incorporation of Chimeric Gag Protein into Retroviral Particles," Journal of Virology, Sep. 1990, vol. 64, No. 9, pp. 4169-4179.
Wilk et al., "Organization of Immature Human Immunodeficiency Virus Type 1," Journal of Virology, 2001, vol. 75(2), pp. 759-771.
Xiong et al. "Sindbis virus: an efficient, broad host range vector for gene expression in animal cells," Science, Mar. 3, 1989, vol. 243, No. 4895, pp. 1188-1191.
Zeng et al. "MHC Class II-Restricted Tumor Antigens Recognized by CD4+ T Cells: New Strategies for Cancer Vaccine Design," Journal of Immunotherapy, 2001, vol. 24, No. 3, pp. 195-204.
Zitvogel et al. "Eradication of established murine tumors using a novel cell-free vaccine: dendritic cell-derived exosomes," Nature Medicine, May 1998, vol. 4, No. 5, pp. 594-600.
International Search Report and Written Opinion for International (PCT) Patent Application No. PCT/US2014/070552, mailed Jun. 26, 2015 19 pages.
International Preliminary Report on Patentability for International (PCT) Patent Application No. PCT/US2014/070552, mailed Jun. 30, 2016 14 pages.
Official Action for Australia Patent Application No. 2014365777, dated Jun. 7, 2019 3 pages.
Notice of Acceptance for Australia Patent Application No. 2014365777, dated Jun. 10, 2020 3 pages.
Official Action with English Translation for Brazil Patent Application No. BR112016013804-0, dated May 3, 2021 21 pages.
Official Action for Canada Patent Application No. 2,934,075, dated Jul. 4, 2017 5 pages.
Official Action for Canada Patent Application No. 2,934,075, dated Aug. 1, 2018 5 pages.
Official Action for Canada Patent Application No. 2,934,075, dated Sep. 3, 2019 4 pages.
Official Action for Canada Patent Application No. 2,934,075, dated Jul. 27, 2021 5 pages.
English Translation of Official Action for China Patent Application No. 201480074163.2, dated Mar. 5, 2019 10 pages.
English Translation of Official Action for China Patent Application No. 201480074163.2, dated Jul. 6, 2020 7 pages.
English Translation of Official Action for China Patent Application No. 201480074163.2, dated Apr. 7, 2021 9 pages.
Official Action with English Translation for China Patent Application No. 202110829496.3, dated Jun. 17, 2022 14 pages.
Official Action for European Patent Application No. 14824680.4, dated Feb. 1, 2018 3 pages.
Summons to Attend Oral Proceedings for European Patent Application No. 14824680.4, dated Jul. 22, 2019 4 pages.
Extended Search Report for European Patent Application No. 20150087.3, dated May 8, 2020 9 pages.
Intention to Grant for European Patent Application No. 20150087.3, dated Mar. 9, 2021 45 pages.
Extended Search Report for European Patent Application No. 21190529.4, dated Feb. 14, 2022 6 pages.
Official Action for India Patent Application No. 201617023312, dated Jul. 30, 2019 9 pages.
Official Action with English Translation for Japan Patent Application No. 2016-558546, dated Oct. 30, 2018 10 pages.
Official Action with English Translation for Japan Patent Application No. 2016-558546, dated Sep. 10, 2019 10 pages.
Official Action with English Translation for Japan Patent Application No. 2016-558546, dated Feb. 12, 2020 10 pages.
Official Action with English Translation for Japan Patent Application No. 2016-558546, dated Aug. 4, 2020 8 pages.
Official Action with English Translation for Japan Patent Application No. 2020-001954, dated Jan. 4, 2022 10 pages.
Official Action with English Translation for Korea Patent Application No. 10-2016-7019097, dated Oct. 6, 2021 15 pages.

(56) References Cited

OTHER PUBLICATIONS

Official Action for Mexico Patent Application No. MX/a/2016/007726, dated Jul. 4, 2019 6 pages.
Official Action for Mexico Patent Application No. MX/a/2016/007726, dated Jul. 22, 2020 6 pages.
Official Action with English Summary for Mexico Patent Application No. MX/a/2016/007726, dated Apr. 16, 2021 5 pages.
Search Report and Written Opinion for Singapore Patent Application No. 11201604868Y, dated May 11, 2017 13 pages.
Official Action for Singapore Patent Application No. 11201604868Y, dated Mar. 16, 2018 3 pages.
Official Action for Singapore Patent Application No. 11201604868Y, dated Sep. 7, 2018 5 pages.
Official Action for U.S. Appl. No. 15/104,785, mailed Jun. 9, 2017 9 pages Restriction Requirement.
Official Action for U.S. Appl. No. 15/104,785, dated Apr. 17, 2018 12 pages.
Official Action for U.S. Appl. No. 15/104,785, dated Dec. 20, 2018 17 pages.
Official Action for U.S. Appl. No. 15/104,785, dated Mar. 30, 2020 20 pages.
Official Action for U.S. Appl. No. 15/104,785, dated Dec. 11, 2020 16 pages.
Official Action for U.S. Appl. No. 17/120,497, dated Mar. 22, 2022 23 pages.
Official Action for U.S. Appl. No. 17/120,497, dated Dec. 1, 2022 11 pages.
Notice of Allowance for U.S. Appl. No. 17/120,497, dated Mar. 15, 2023 9 pages.
Bloom et al. "Self-amplifying RNA vaccines for infectious diseases," Gene Therapy, 2021, vol. 28, pp. 117-129.
Official Action with English Translation for China Patent Application No. 202110829496.3, dated Jan. 18, 2023 18 pages.
English Translation of Official Action for Japan Patent Application No. 2020-001954, dated Aug. 9, 2022 10 pages.
Official Action with English Translation for Japan Patent Application No. 2020-001954, dated Apr. 4, 2023 3 pages.
Official Action with English Translation for Brazil Patent Application No. BR112016013804-0, dated Jun. 7, 2023 12 pages.

\* cited by examiner

SEQUENCE LISTING

Sequence total quantity: 1
SEQ ID NO: 1          moltype = DNA  length = 11913
FEATURE              Location/Qualifiers
source               1..11913
                     mol_type = other DNA
                     organism = synthetic construct
SEQUENCE: 1

```
gacggatcgg gagatctccc gatccctat ggtgcactct cagtacaatc tgctctgatg   60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aatgtcgta acaactccgc cccattgacg caaatgggcg  780
gtaggcgtgt acggtgggag gtctatataa gcagagctcg tatgacata ttgtcgttag  840
aacgcggcta caattaatac ataacttat gtatcataca catacgattt aggggacact  900
atagattgac ggcgtagtac acactattga atcaaacagc cgaccaattg cactaccatc  960
acaatggaga agccagtagt aaacgtagac gtagaccccc agagtccgtt tgtcgtcaa  1020
ctgcaaaaaa gcttcccgca atttgaggta gtagcacagc aggtcactcc aaatgaccat  1080
gctaatgcca gagcatttc gcatctggcc agtaaactaa tcgagctgga ggttcctacc  1140
acagcgacga tcttggacat aggcagcgca ccggctcgta gaatgttttc cgagcaccag  1200
tatcattgtg tctgccccat gcgtagtcca gaagacccgg accgcatgat gaaatacgcc  1260
agtaaactgg cggaaaaagc gtgcaagatt acaaacaaga acttgcatga gaagattaag  1320
gatctccgga ccgtactttga tacgccggat gctgaaacac catcgctctg ctttcacaac  1380
gatgttacct gcaacatgcg tgccgaatat tccgtcatgc aggacgtgta tatcaacgct  1440
cccggaacta tctatcatca ggctatgaaa ggcgtgcgga ccctgtactg gattggcttc  1500
gacaccaccc agttcatgtt ctcggctatg gcaggttcgt accctgcgta caacaccaac  1560
tgggccgacg agaaagtcct tgaagcgcgt aacatcggac tttgcagcac aaagctgagt  1620
gaaggtagga caggaaaatt gtcgataatg aggaagaagg agttgaagcc cgggtcgcgg  1680
gtttatttct ccgtaggatc gacactttat ccagaacaca gagccagctt gcagggctgg  1740
catcttccat cggtgttcca cttgaatgga aagcagtcgt acacttgccg ctgtgataca  1800
gtggtgagtt gcgaaggcta cgtagtgaag aaaatcacca tcagtcccgg gatcacggga  1860
gaaaccgtgg gatacgcgt tacacacaat agcgagggct tcttgctatg caaagttact  1920
gacacagtaa aaggagaacg ggtatcgttc cctgtgtgca cgtacatccc ggccaccata  1980
tgcgatcaga tgactggtat aatggccacg gatatatcac ctgacgatgc acaaaaactt  2040
```

```
ctggttgggc tcaaccagcg aattgtcatt aacggtagga ctaacaggaa caccaacacc   2100
atgcaaaatt accttctgcc gatcatagca caagggttca gcaaatgggc taaggagcgc   2160
aaggatgatc ttgataacga gaaaatgctg ggtactagag aacgcaagct tacgtatggc   2220
tgcttgtggg cgtttcgcac taagaaagta cattcgtttt atcgcccacc tggaacgcag   2280
acctgcgtaa aagtcccagc ctcttttagc gcttttccca tgtcgtccgt atggacgacc   2340
tctttgccca tgtcgctgag gcagaaattg aaactggcat tgcaaccaaa gaaggaggaa   2400
aaactgctgc aggtctcgga ggaattagtc atggaggcca aggctgcttt tgaggatgct   2460
caggaggaag ccagagcgga gaagctccga gaagcacttc caccattagt ggcagacaaa   2520
ggcatcgagg cagccgcaga agttgtctgc gaagtggagg ggctccaggc ggacatcgga   2580
gcagcattag ttgaaacccc gcgcggtcac gtaaggataa tacctcaagc aaatgaccgt   2640
atgatcggac agtatatcgt tgtctcgcca aactctgtgc tgaagaatgc caaactcgca   2700
ccagcgcacc cgctagcaga tcaggttaag atcataacac actccggaag atcaggaagg   2760
tacgcggtcg aaccatacga cgctaaagta ctgatgccag caggaggtgc cgtaccatgg   2820
ccagaattcc tagcactgag tgagagcgcc acgttagtgt acaacgaaag agagtttgtg   2880
aaccgcaaac tataccacat tgccatgcat ggccccgcca agaatacaga agaggagcag   2940
tacaaggtta caaaggcaga gcttgcagaa acagagtacg tgtttgacgt ggacaagaag   3000
cgttgcgtta agaaggaaga agcctcaggt ctggtcctct cggagaact gaccaaccct   3060
ccctatcatg agctagctct ggagggactg aagacccgac ctgcggtccc gtacaaggtc   3120
gaaacaatag gagtgatagg cacaccgggg tcgggcaagt cagctattat caagtcaact   3180
gtcacggcac gagatcttgt taccagcgga aagaaagaaa attgtcgcga aattgaggcc   3240
gacgtgctaa gactgagggg tatgcagatt acgtcgaaga cagtagattc ggttatgctc   3300
aacggatgcc acaaagccgt agaagtgctg tacgttgacg tgccacgca   3360
ggagcactac ttgccttgat tgctatcgtc aggcccgca agaaggtagt actatgcgga   3420
gaccccatgc aatgcggatt cttcaacatg atgcaactaa aggtacattt caatcaccct   3480
gaaaagaca tatgcaccaa gacattctac aagtatatct cccggcgttg cacacagcca   3540
gttacagcta ttgtatcgac actgcattac gatggaaaga tgaaaaccac gaacccgtgc   3600
aagaagaaca ttgaaatcga tattacaggg gccacaaagc cgaagccagg ggatatcatc   3660
ctgcacatgtt tccgcgggtg ggttaagcaa ttgcaaatcg actatcccgg acatgaagta   3720
atgacagccg cggcctcaca agggctaacc agaaaaggag tgtatgccgt ccggcaaaaa   3780
gtcaatgaaa acccactgta cgcgatcaca tcagagcatg tgaacgtgtt gctcaccgc   3840
actgaggaca ggctagtgtg gaaaacttg cagggcgacc catggattaa gcagccact    3900
aacatacta aaggaaactt tcaggctact atagaggact gggaagctga acacaaggga   3960
ataattgcta caataaacag ccccactccc cgtgccaatc cgttcagctg caagaccaac   4020
gtttgctggg cgaaagcatt ggaaccgata ctagccacgg ccggtatcgt acttaccggt   4080
tgccaggtga gcgaactgtt cccacagttt gcggatgaca aaccacattc ggccatttca   4140
gccttagacg taatttgcat taagttttt ggcatggact tgacaagcgg actgtttct    4200
aaaacagagca tcccactaac gtaccatccc gccgattcag cgaggccggt agctcattgg   4260
gacaacagcc caggaacccg caagtatggg tacgatcacg ccattgccgc cgaactctcc   4320
cgtagatttc cggtgttcca gctagctggg aagggcacac aatttgattt gcagacgggg   4380
agaaccagag ttatctctgc acagcataac ctggtcccgg tgaaccgcaa tcttcctcac   4440
gccttagtcc ccgagtacaa ggagaagcaa ccggccggg tcaaaaaatt cttgaaccag   4500
ttcaaacacc actcagtact tgtggtatca gaggaaaaaa ttgaagctcc ccgtaagaga   4560
atcgaatgga tcgccccgat tggcatagcc ggtgcagata gaactacaa cctggcttc    4620
gggtttccgc cgcaggcacg gtacgacctg gtgttcatca acattggaac taaatacaga   4680
aaccaccact tcagcagtg cgaagaccat gcggcgacct taaaaaccct ttcgcgttcg   4740
gccctgaatt gccttaaccc aggaggcacc ctcgtggtga gtcctatgg ctacgccgac    4800
cgcaacagtg aggacgtagt caccgctctt gccagaaagt ttgtcagggt gtctgcagcg   4860
agaccagatt gtgtctcaag caatacgaaa atgtacctga ttttccgaca actagacaac   4920
agccgtacac ggcaattcac cccgcaccat ctgaattgcg tgatttcgtc cgtgtatgag   4980
ggtacaagag atgagttgg agccgcgccg tcataccgca ccaaaaggga gaatattgct   5040
gactgtcaag aggaagcagt tgtcaacgca gccaatccgc tgggtagacc aggcgaagga   5100
gtctgccgtg ccatctataa acgttggccg accagttta ccgattcagc cacggagaca   5160
ggcaccgcaa gaatgactgt gtgcctagga aagaagtga tccacgcggt cggccctgat   5220
ttccggaagc acccagaagc agaagccttg aaattgctac aaaacgccta ccatgcagtg   5280
gcagacttag taaatgaaca taacatcaag tctgtcgcca ttccactgct atctacaggc   5340
atttacgcag ccggaaaaga ccgccttcga gtatcacta actgcttgac aaccgcgcta   5400
gacagaactg acgcggacgt aaccatctat tgcctggata aaagtggaa ggaaagaatc   5460
gacgcggcac tccaacttaa ggagtctgta acagagctga aggatgaaga tatggagatc   5520
gacgatgagt tagtatggat tcatccagac agttgcttga gcggaagaaa gggattcagt   5580
actacaaaag gaaaattgta ttcgtacttc gaaggcacca aattccatca agcagcaaaa   5640
gacatgcgg agataaaggt cctgttccct aatgaccagg aaagtaatga acaactgtgt   5700
gcctacatat tgggtgagac catggaagca atccgcgaaa agtgcccggt cgaccataac   5760
ccgtcgtcta gcccgccaaa aacgttgccg tgcctttgca tgtatgccat gacgccagaa   5820
agggtccaca gacttagaag caataacgtc aagaagtta cgatgctc ctccaccccc    5880
cttcctaagc acaaaattaa gaatgttcag aaggttcagt gcacgaaagt agtcctgttt   5940
aatccgcaca ctcccgcatt cgttcccgcc cgtaagtaca tagaagtgcc agaacagcct   6000
accgctcctc ctgcacaggc cgaggaggcc ccgaagttg tagcgacacc gtcaccatct   6060
acagctgata cacctcgct tgatgtcaca gacatctcac tggatatgga tgacagtagc   6120
gaaggctcac tttttcgag ctttagcgga tcggacaact ctattactag tatggacagt   6180
tggtcgtcag gacctagttc actagagata gtagaccgaa ggcaggtggt ggtggctgac   6240
gttcatgccg tccaagagcc tgccctatt ccaccgccaa ggctaaagaa gatggccgc     6300
ctggcagcgg caagaaaaga gcccactcca ccggcaagca atagctctga gtccctccac   6360
ctctcttttg gtgggtatc catgtccctc ggatcaattt tcgacggaga cggccgc       6420
caggcaggag tacaaccgct ggcaacaggc tgcctatgtc ttcggatcg                6480
ttttccgacg gaagagatga tgagctgagc gcagagtaa ctgagtccga acccgtcctg   6540
tttggatcat ttgaaccggg cgaagtgaac tcaattatat cgtcccgatc agccgtatct   6600
tttccactac gcaagcagag acgtagacgc aggagcagga ggactgaata ctgactaacc   6660
ggggtaggtg ggtacatatt ttcgacggac acaggccctg gcacttgca aaagaagtcc   6720
gttctgcaga accagcttac agaaccgacc ttggagcgca atgtcctgga aagaattcat   6780
```

```
gccccggtgc tcgacacgtc gaaagaggaa caactcaaac tcaggtacca gatgatgccc  6840
accgaagcca acaaaagtag gtaccagtct cgtaaagtag aaaatcagaa agccataacc  6900
actgagcgac tactgtcagg actacgactg tataactctg ccacagatca gccagaatgc  6960
tataagatca ccctatccgaa accattgtac tccagtagcg taccggcgaa ctactccgat  7020
ccacagttcg ctgtagctgt ctgtaacaac tatctgcact agaactatcc gacagtagca  7080
tcttatcaga ttactgacga gtacgatgct tacttggata tggtagacgg gacagtcgcc  7140
tgcctggata ctgcaacctt ctgccccgct aagcttagaa gttacccgaa aaaacatgag  7200
tatagagccc cgaatatccg cagtgcggtt ccatcagcga tgcagaacac gctacaaaat  7260
gtgctcattg ccgcaactaa aagaaattgc aacgtcacgc agatgcgtga actgccaaca  7320
ctggactcag cgacattcaa tgtcgaatgc tttcgaaaat atgcatgtaa tgacgagtat  7380
tgggaggagt tcgctcggaa gccaattagg attaccactg agtttgtcac cgcatatgta  7440
gctagactga aaggccctaa ggccgccgca ctatttgcaa agacgtataa tttggtccca  7500
ttgcaagaag tgcctatgga tagattcgtc atggacatga aaagagacgt gaaagttaca  7560
ccaggcacga aacacacaga agaaagaccg aaagtacaag tgatacaagc cgcagaaccc  7620
ctggcgactg cttacttatg cgggattcac cgggaattag tgcgtaggct tacggccgtc  7680
ttgcttccaa acattcacac gcttttttgac atgtcggcgg aggatttttga tgcaatcata  7740
gcagaacact tcaagcaagg cgacccggta ctggagacgg atatcgcatc attcgacaaa  7800
agccaagacg acgctatggc gttaaccggt ctgatgatct tggaggacct gggtgtggat  7860
caaccactac tcgacttgat cgagtgcgcc tttggagaaa tatcatccac ccatctacct  7920
acgggtactc gttttaaatt cggggcgatg atgaaatccg gaatgttcct cacacttttt  7980
gtcaacacag ttttgaatgt cgttatcgcc agcagagtac tagaagagcg gcttaaaacg  8040
tccagatgtg cagcgttcat tggcgacgac aacatcatac atggagtagt atctgacaaa  8100
gaaatggctg agaggtgcgc cacctggctc aacatggagg ttaagatcat cgacgcagtc  8160
atcggtgaga gaccaccctta cttctgcggc ggatttatct tgcaagattc ggttacttcc  8220
acagcgtgcc gcgtggcgga tcccctgaaa aggctgttta agttgggtaa accgctccca  8280
gccgacgaca gcaagacga agacagaaga cgcgctctgc tagatgaaaa aaaggcgtgg  8340
tttagagtag gtataacagg cactttagca gtgccgtga cgacccggta tgaggtagac  8400
aatattacac ctgtcctact ggcattgaga acttttgccc agagcaaaag agcattccaa  8460
gccatcagag gggaaataaa gcatctctac ggtggtccta aatagtcagc atagtacatt  8520
tcatctgact aatactacaa caccaccacc tctagagctt gccgccacca tggtgagcaa  8580
gggcgaggag ctgttcaccg gggtggtgcc catcctggtc gagctggacg gcgacgtgaa  8640
cggccacaag ttcagcgtgt ccggcgaggg cgagggcgat gccacctacg gcaagctgac  8700
cctgaagttc atctgcacca ccggcaagct gcccgtgccc tggcccaccc tcgtgaccac  8760
cctgacctac ggcgtgcagt gcttcagccg ctaccccgac cacatgaagc agcacgactt  8820
cttcaagtcc gccatgcccg aaggctacgt ccaggagcgc accatcttct tcaaggacga  8880
cggcaactac aagacccgcg ccgaggtgaa gttcgagggc gacaccctgg tgaaccgcat  8940
cgagctgaag ggcatcgact tcaaggagga cggcaacatc ctggggcaca gctggagta  9000
caactacaac agccacaacg tctatatcat ggccgacaag cagaagaacg gcatcaaggt  9060
gaacttcaag atccgccaca acatcgagga cggcagcgtg cagctcgccg accactacca  9120
gcagaacacc cccatcggcg acggccccgt gctgctgccc gacaaccact acctgagcac  9180
ccagtccgcc ctgagcaaag accccaacga gaagcgcgat cacatggtcc tgctggagtt  9240
cgtgaccgcc gccgggatca ctcacggcat ggacgagctg tacaagtaaa gcggccgtga  9300
gcatgcaggc cttgggccca atgatccgac cagcaaaact cgatgtactt ccgaggaact  9360
gatgtgcata atgcatcagg ctggtacatt agatccccgc ttaccgcggg caatatagca  9420
acactaaaaa ctcgatgtac ttccgaggaa gcgcagtgca taatgctgcg cagtgttgcc  9480
acataaccac tatattaacc atttatctag cggacgccaa aaactcaatg tatttctgag  9540
gaagcgtggt gcataatgcc acgcagcgtc tgcataactt ttattatttc ttttattaat  9600
caacaaaatt ttgttttttaa catttcaaaa aaaaaaaaaa aaaaaaaaaa aaaaaaaaaa  9660
aaagggaatt cctcgattaa ttaagcggcc gctcgagatg gcacgcgtgt tacgttttta  9720
ccgtcgacct ctagctagag cttggcgtaa tcatggtcat agctgtttcc tgtgtgaaat  9780
tgttatccgc tcacaattcc acacaacata cgagccgaa gcataaagtg taaagcctgg  9840
ggtgcctaat gagtgagcta actcacatta attgcgttgc gctcactgcc cgctttccag  9900
tcgggaaacc tgtcgtgcca gctgcattaa tgaatcggcc aacgcgcggg gagaggcggt  9960
ttgcgtattg ggcgctcttc cgcttcctcg ctcactgact cgctgcgctc ggtcgttcgg 10020
ctgcggcgag cggtatcagc tcactcaaag gcggtaatac ggttatccac agaatcaggg 10080
gataacgcag gaaagaacat gtgagcaaaa ggccagcaaa aggccaggaa ccgtaaaaag 10140
gccgcgttgc tggcgttttt ccataggctc cgcccccctg acgagcatca caaaaatcga 10200
cgctcaagtc agaggtggcg aaacccgaca ggactataaa gataccaggc gtttccccct 10260
ggaagctccc tcgtgcgctc tcctgttccg accctgccgc ttaccggata cctgtccgcc 10320
tttctccctt cgggaagcgt ggcgctttct catagctcac gctgtaggta tctcagttcg 10380
gtgtaggtcg ttcgctccaa gctgggctgt gtgcacgaac cccccgttca gcccgaccgc 10440
tgcgccttat ccggtaacta tcgtcttgag tccaacccgg taagacacga cttatcgcca 10500
ctggcagcag ccactggtaa caggattagc agagcgaggt atgtaggcgg tgctacagag 10560
ttcttgaagt ggtggcctaa ctacggctac actagaagaa cagtatttgg tatctgcgct 10620
ctgctgaagc cagttacctt cggaaaaaga gttggtagct cttgatccgg caaacaaacc 10680
accgctggta gcggtggttt ttttgtttgc aagcagcaga ttacgcgcag aaaaaaagga 10740
tctcaagaag atcctttgat cttttctacg ggtctgacg ctcagtggaa cgaaaactca 10800
cgttaaggga ttttggtcat gagattatca aaaaggatct tcacctagat ccttttaaat 10860
taaaaatgaa gttttaaatc aatctaaagt atatatgagt aaacttggtc tgacagttac 10920
caatgcttaa tcagtgaggc acctatctca gcgatctgtc tatttcgttc atccatagtt 10980
gcctgactcc ccgtcgtgta gataactacg atacgggagg gcttaccatc tggccccagt 11040
gctgcaatga taccgcgaga cccacgctca ccggctccag atttatcagc aataaaccag 11100
ccagccggaa gggccgagcg cagaagtggt cctgcaactt tatccgcctc catccagtct 11160
attaattgtt gccgggaagc taatagtaagt agttcgccag ttaatagttt cgcaacgttg 11220
gttgccattg ctacaggcat cgtggtgtca cgctcgtcgt ttggtatggc ttcattcagc 11280
tccggttccc aacgatcaag gcgagttaca tgatccccca tgttgtgcaa aaaagcggtt 11340
agctccttcg gtcctccgat cgttgtcaga agtaagttgg ccgcagtgtt atcactcatg 11400
gttatggcag cactgcataa ttctcttact gtcatgccat ccgtaagatg cttttctgtg 11460
actggtgagt actcaaccaa gtcattctga gaatagtgta tgcggcgacc gagttgctct 11520
```

-continued

```
tgcccggcgt caatacggga taataccgcg ccacatagca gaactttaaa agtgctcatc  11580
attggaaaac gttcttcggg gcgaaaactc tcaaggatct taccgctgtt gagatccagt  11640
tcgatgtaac ccactcgtgc acccaactga tcttcagcat cttttacttt caccagcgtt  11700
tctgggtgag caaaaacagg aaggcaaaat gccgcaaaaa agggaataag ggcgacacgg  11760
aaatgttgaa tactcatact cttccttttt caatattatt gaagcattta tcagggttat  11820
tgtctcatga gcggatacat atttgaatgt atttagaaaa ataaacaaat aggggttccg  11880
cgcacatttc cccgaaaagt gccacctgac gtc                              11913
```

CANCER IMMUNOTHERAPY BY DELIVERING CLASS II MHC ANTIGENS USING A VLP-REPLICON

CROSS REFERENCE TO RELATED APPLICATIONS

This application is a divisional of U.S. patent application Ser. No. 17/120,497, filed Dec. 14, 2020, which is a divisional of U.S. patent application Ser. No. 15/104,785, filed Jun. 15, 2016; which is a national stage application under 35 U.S.C. 371 and claims the benefit of PCT Application No. PCT/US2014/070552 having an international filing date of Dec. 16, 2014, which designated the United States; which PCT application claims benefit of under 35 U.S.C. § 119(e) of U.S. Provisional Patent Application No. 61/916,394, filed Dec. 16, 2013; the disclosure of each of which is incorporated herein by reference in their entirety.

REFERENCE TO SEQUENCE LISTING

This application contains a Sequence Listing submitted as a XML file named "10672NCI-40-PUS-D2.xml", having a size in bytes of 13,960 bytes, and created on Feb. 24, 2023. The information contained in this electronic file is hereby incorporated by reference in its entirety pursuant to 37 CFR § 1.52(e)(5).

TECHNICAL FIELD

The invention described herein relates to delivering and transcribing nucleic acid expressing class II major histocompatibility antigens to mammals using replication-defective virus-like particles.

BACKGROUND

A major challenge in cancer therapy, particularly chemotherapy, is the lack of specificity for target cancer cells as the small molecules are administered systemically and affect all cells with high mitotic index resulting in detrimental side effects. Antibody based therapies display improved specificity for target cells but result in low efficacy. Monoclonal antibodies (mAb) constitute one of the largest classes of reagents or drugs. The current global market for mAbs is more than $36 billion (Ledford, 2020, Nature 468:18-19). Current strategies for antibody based cancer therapy are limited to only a handful of extracellular proteins or receptors (Baker, 2005, Nature Biotech, 23:1065-72; Cohen, et al. 2009, MAbs, 1:56-66), which are accessible and expressed on the outer membranes of cancer cells. Because they are accessible, it was possible to generate antibodies against them. Examples include rituximab (RITUXAN® or MABTHERA®) an anti-CD20 monoclonal antibody (mAb) to treat lymphoma, trastuzumab (HERCEPTIN®) an anti-Her2 mAb to treat some breast cancers and cetuximab (ERBITUX®) an anti-FGF receptor mAb to treat head-neck and colorectal cancers (Adams, 2005, Nature Biotech, 23:1147-57). They are proven to be effective agents for recognizing and destroying cancer cells. However, there are no new accessible cancer markers on cancer cells surface, which limits the future Ab repertoire which can be generated.

There is an unmet need to exploit a large untapped source of intracellular cancer antigens for cancer therapy. Examples of such intracellular cancer therapeutic targets include: Ras mutants, phosphatases, kinases transcription factors, alpha fetoprotein (AFP), CA15-3, CA27-29, CA19-9, CA-125, calcitonin, calretinin, carcinoembryonic antigen, chromogranin, cytokeratin, desmin, epithelial membrane protein (EMA), Factor VIII, CD31, FL1, glial fibrillary acidic protein (GFAP), gross cystic disease fluid protein (GCDFP-15), HMB-45, human chorionic gonadotropin (hCG), inhibin, keratin, lymphocyte marker, MART-1 (Melan-A), Myo D1, muscle-specific actin (MSA), neurofilament, neuron-specific enolase (NSE), placental alkaline phosphatase (PLAP), prostate-specific antigen, PTPRC (CD45), S100 protein, smooth muscle actin (SMA), synaptophysin, thyroglobulin, thyroid transcription factor-1, tumor M2-PK, vimentin, cluster of differention 10 (CD10), CD13, CD15, CD20, CD25, CD28, CD30, CD34, CD99, and CD117. Intracellular cancer antigens are not accessible to antibodies and therefore it is more difficult to treat cancer patients with antibodies against these antigens as they may not reach the intracellular location because of large size of the antibodies.

One approach is to bring those cancer antigens out and display on the tumor cells surface to convert them into induced antigen presenting cells (iAPC) and generate cancer vaccines against the tumor cells, thereby teaching tumor cells to activate cellular machinery to make antibodies against them. It is known that tumor cells synthesize multiple proteins that are potential immunogens and processed peptides from these proteins will activate an antitumor response in the patient. Transfected tumor cells will present those antigens to T(CD4+) helper and activate cytolytic T lymphocytes (CD8+ cells) and generate effector and immune memory T cells effectively generating a cancer vaccine, which is likely to be essential for protection from metastasis—the main cause of cancer death. The attractiveness of this approach for cancer therapy is there is no need for prior knowledge of the cancer antigen(s). Thus, it might work for any type cancer causing protein or antigen. Cancer vaccines are a promising tool for cancer treatment and prevention because of their potential for inducing tumor specific responses in conjunction with minimal toxicity for healthy cells.

A mouse HLA/CD80 in mouse (autologous) system has been found to prolong survival (Armstrong, et al., 1997, Proc Natl Acad Sci, 94:6886-91; Humphreys, et al., 2004, Cell Mol Immunol, 1:180-85). This system requires isolating tumor cells, propagating the tumor cells, modifying the cells (ex vivo) with a recombinant retrovirus containing these genes, and re-implanting these cells into mice to study immunotherapy. The procedure is cumbersome, lengthy, and susceptible to contamination during ex vivo steps. Further, the reported results are based on genetically and syngeneic, immunologically identical systems. The use of retrovirus creates a chance to retroviral integration in the host genome at a position that could be potentially dangerous.

There is a need to develop a means of producing a gene therapy that does not have the shortcomings of an ex vivo procedure, and which does not require use of a retrovirus that can harm the host.

SUMMARY

What is described is a novel methodology for inducible immunotherapy of cancer. This immunotherapy is directed to coexpressing class II major histocompatibility (MHC) antigens within the tumor cells of a patient to boost the immune response to the tumor antigens. The transfected cells will act as antigen presenting cells. What was discovered is that the MHC antigens expressed in the transfected tumor cells induces an immune reaction directed against the tumor antigens by acting as antigen presenting molecules. The immune response directed against the tumor cells will then be elaborated by the presence of tumor antigens presented the host antigen presenting cells. What is also described is a virus like particle (VLP) containing RNA coding for MHC class II antigens along with the tumor antigen that can be administered to an animal, which induce host cells of the animal to express these antigens. The VLP mediated RNA delivery system has been previously described in WO 2013148302, hereby incorporated by reference in its entirety, and therein shown to be efficient in expressing proteins in mammalian cells.

What is described is a method of preventing or treating a disease in a mammalian subject, comprising administering to the subject who is need thereof an effective dosage of a pharmaceutical composition comprising a VLP comprising:
  a. an alphavirus replicon comprising a recombinant polynucleotide, wherein the polynucleotide comprises a sequence encoding both subunits of a class II major histocompatibility antigen,
  b. a retroviral gag protein, and
  c. a fusogenic envelope protein,
wherein the VLP does not contain an alphavirus structural protein gene. The recombinant polypeptide may further comprise a sequence encoding a costimulatory signal protein. The costimulatory signal protein is preferably selected from the group consisting of CD28, CD80, CD86, and CTLA-4. The costimulatory signal protein more preferably comprises CD80.

The method described herein may be directed to preventing or treating a disease in which the patient has a tumor. The patient may be a cancer patient, preferably a cancer patient is selected from the group of cancer patients having solid tumors derived from breast, cervical, prostate, ovary, renal carcinoma, lung, gastric, pancreas, glioblastoma, and colorectal, most preferably a breast cancer patient. The recombinant polynucleotide accordingly may further comprise a sequence encoding a tumor-specific antigen, preferably a polypeptide selected from the group consisting of AFP, CA15-3, CA27-29, CA19-9, CA-125, calcitonin, calretinin, carcinoembryonic antigen, chromogranin, cytokeratin, desmin, EMA, Factor VIII, FL1, GFAP, GCDFP-15, HMB-45, hCG, inhibin, keratin, lymphocyte marker, MART-1 (Melan-A), Myo D1, MSA, neurofilament, NSE, PLAP, prostate-specific antigen, S100 protein, SMA, synaptophysin, thyroglobulin, thyroid transcription factor-1, tumor M2-PK, vimentin, CD10, CD13, CD15, CD20, CD25, CD30, CD31, CD34, CD45 (PTPRC), CD99, CD117, and a fragment thereof.

The method described herein may be directed to preventing or treating an infectious disease. The recombinant polypeptide accordingly may further comprise a sequence of an infectious agent. The infectious agent may be an infectious virus.

The VLP of the method described herein may comprise an alphavirus replicon derived from Sindbis virus or Venezuelan equine encephalitis virus. The fusogenic envelope protein of the VLP may comprise a glycoprotein, or fragment or derivative thereof. The fusogenic envelope protein may specifically bind to a tumor cell. The VLP accordingly may be capable of binding to a eukaryotic cell. The eukaryotic cell may be a human cell. The binding may be specific to a target cell.

The method described herein may administer the pharmaceutical composition parenterally. The pharmaceutical composition may be administered by intravenous injection. The pharmaceutical composition may be administered by injection within the tumor.

In the method described herein the pharmaceutical composition may be administered in combination with a chemotherapeutic drug. The chemotherapeutic drug may be selected from the drug classes consisting of a taxane (paclitaxel or docetaxel), an anthracycline (doxorubicin or epirubicin), cyclophosphamide, capecitabine, tamoxifen, letrozole, carboplatin, gemcitabine, cisplatin, erlotinib, irinotecan, fluorouracil, and oxaliplatin. The pharmaceutical composition may be administered in combination with radiation therapy.

DETAILED DESCRIPTION OF ILLUSTRATIVE EMBODIMENTS

Definitions

Figure 1:
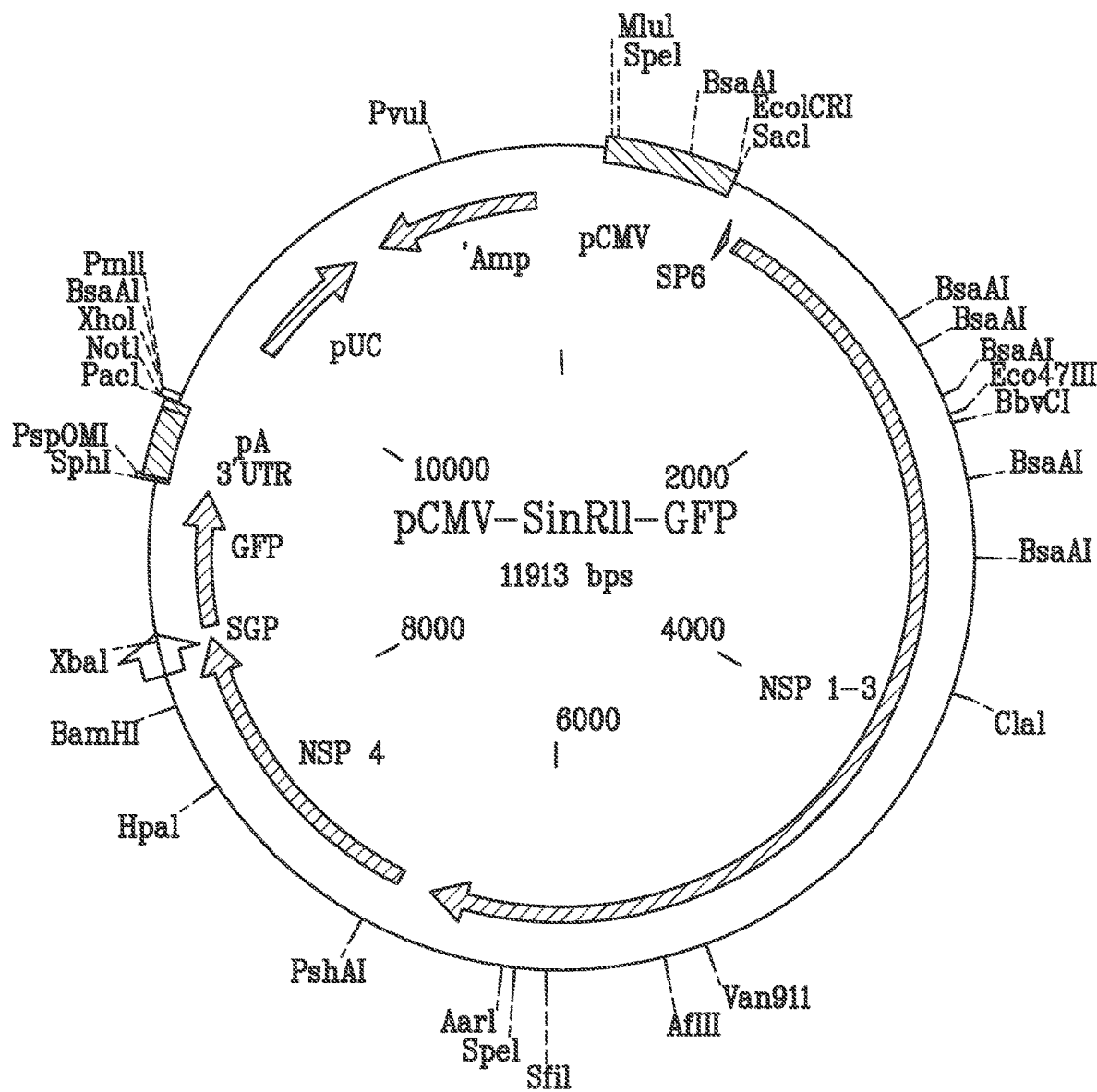
FIG. 1 schematically shows an example of a vector. The DNA sequence of the vector is provided in the Sequence Listing, appended hereto (SEQ ID NO:1).
Figure 2:
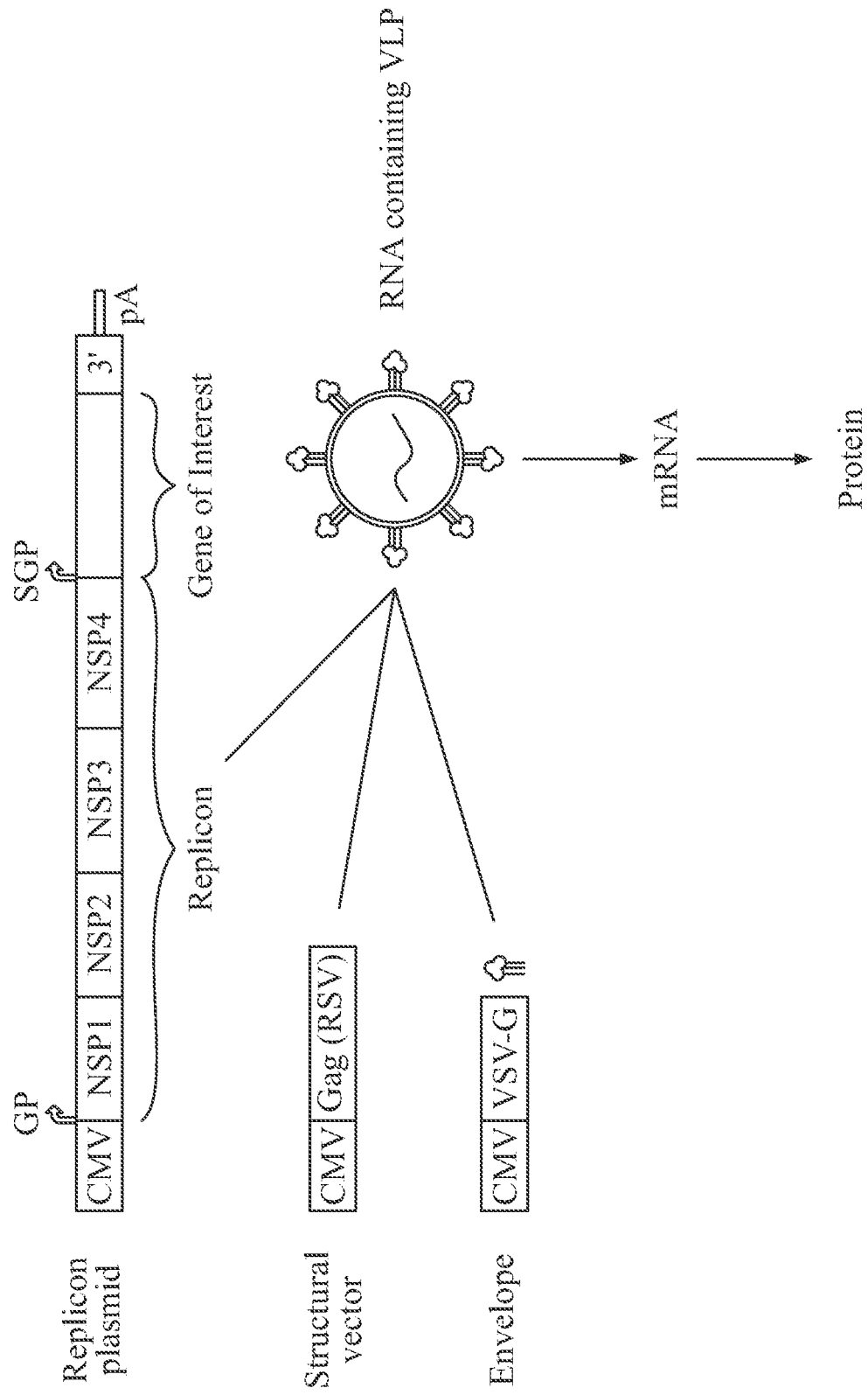
FIG. 2 shows the basic concept for producing and using the VLP described herein. The replicon plasmid contains a CMV promoter driving expression of a replicon and a gene of interest. The replicon contains elements NSP1, NSP2, NSP3 and NSP4. The gene of interest contains a nucleic acid encoding the two class II MEW antigen subunits and a disease-specific antigen. The structural vector contains the Gag from RSV under control of a CMV promoter. The envelope vector contains VSV-G protein under control of a CMV promoter. These are transfected into a producer host cell, which manufactures the RNA containing VLP. The VLP can be used to infect target cells, which produce the proteins encoded by the gene of interest.
Figure 3:
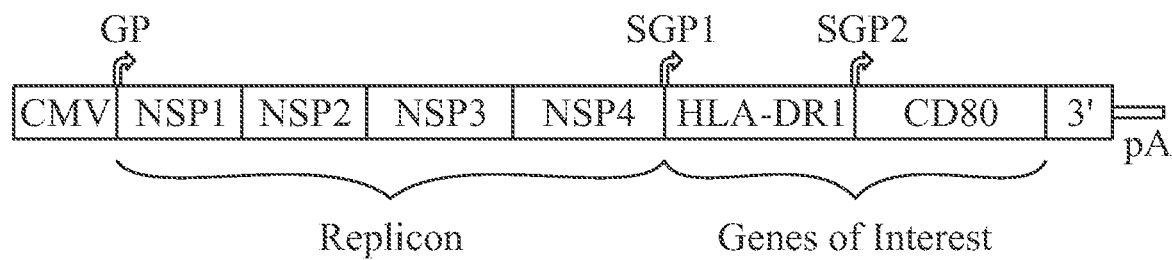
FIG. 3 shows the specific construct of the Examples. This shows the replicon plasmid, VLP-VEE, which contains nucleic acid encoding HLA-DR1 and CD80 protein.
Figure 4:
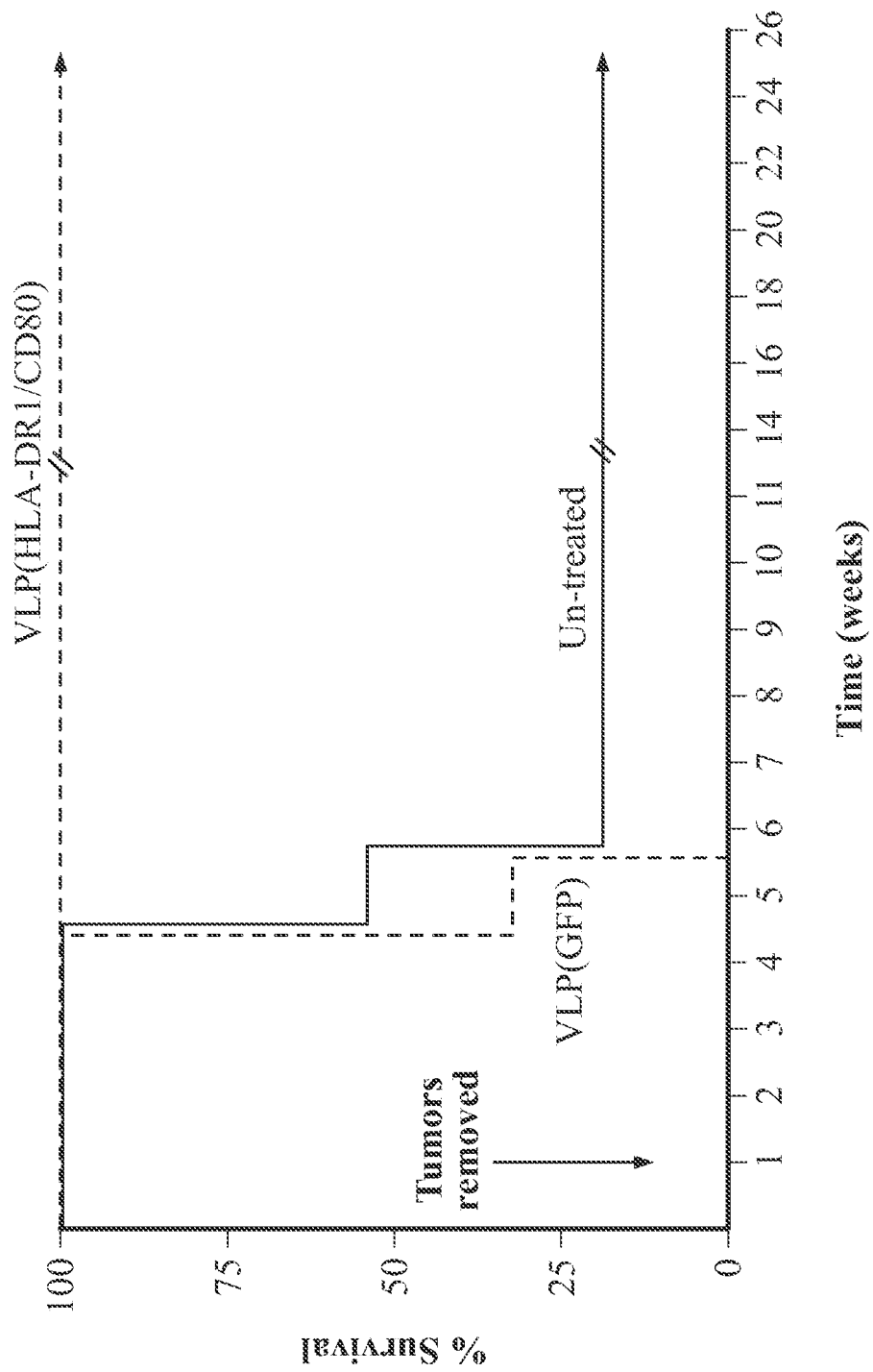
FIG. 4 shows animal survival after 4T1-Luc2 (breast cancer) cell grafting.

When the terms "one," "a," or "an" are used in this disclosure, they mean "at least one" or "one or more," unless otherwise indicated.

The term "fusogenic protein" as used herein is meant to refer to a protein that can induce the fusion of the plasma membrane derived envelope of the VLP to the membrane of the recipient cell.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Replicon" as used herein refers to a polynucleotide having the genetic elements necessary to facilitate replication of its sequence and while also being capable of undergoing translation.

"Virus-like particle" (VLP), as used herein, refers to a structure resembling a virus particle. In preferred embodiments, a VLP contains at least one fusogenic protein displayed on the surface of the particle. A virus-like particle in accordance with the invention lacks all or part of the replicative components of the viral genome. Typically, a virus-like particle in accordance with the invention does not carry genetic information encoding for the proteins of the virus-like particle.

Vectors

Alphaviruses belong to the group IV Togaviridae family of viruses. The alphaviruses are small, spherical, enveloped viruses with a genome of a single positive sense strand RNA. The total genome length ranges between 11,000 and 12,000 nucleotides, and has a 5' cap, and 3' poly-A tail. The four non-structural protein genes (NSP genes) are encoded in the 5' two-thirds of the genome, while the three structural proteins are translated from a subgenomic mRNA colinear with the 3' one-third of the genome.

There are two open reading frames (ORFs) in the alphavirus genome, non-structural and structural. The first includes NSP genes and encodes proteins (nsP1-nsP4) necessary for transcription and replication of viral RNA. The second encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion.

The Sindbis virus (SIN) and Venezuelan equine encephalitis virus (VEEV) are alphaviruses whose genome comprises a positive mRNA strand of 11703 nucleotides. SIN infects a variety of vertebrate hosts. The genome of Sindbis virus encodes nonstructural (NS, replicon) and structural proteins (capsid and pH dependent fusogenic envelope) that are directly translated in the cytoplasm of the host cell. The alphaviruses also include Aura virus, Babanki virus, Barmah Forest virus, Bebaru virus, Cabassou virus, Chikungunya virus, Eastern equine encephalitis virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus, Salmon pancreas disease virus, Semliki Forest virus (SFV), Southern elephant seal virus, Tonate virus, Trocara virus, Una virus, Western equine encephalitis virus, and Whataroa virus.

Infection of host cell with an alphavirus results in cytotoxicity culminating with apoptosis, This is mostly due to both: expression of alphavirus genomic RNA in large quantities triggering antiviral state in host cells and direct interaction of alphaviral non-structural proteins (NSP2 of SIN or NC of VEEV) with cellular mRNA synthesis or translational shut-off causing cytophathic effect (CPE) on host cell host cell. A natural SIN variant containing a point mutation in one of the nonstructural proteins, NSP2 (at position 726) demonstrated sustained and noncytopathic growth in infected cells although the viral titer recovered from infected cells was substantially reduced (Frolov, et al., 1999, J Virol, 73:3845-65).

Alphaviruses are of interest to gene therapy researchers. Ross River virus, SIN, SFV, and VEEV have all been used to develop vectors for gene delivery. Pseudotyped viruses may be formed by combining alphaviral envelopes glycoproteins and retroviral capsids. Alphaviral envelope glycoproteins pseudotyped retroviruses or lentiviruses are able to integrate the genes that they carry into the potential host cells. The pseudotyped alphaviruses are recognized and infected by the alphaviral envelope proteins E2 and E1. Stable integration of viral genes is mediated by retroviral interiors of these vectors.

There are limitations to the use of alphaviruses in the field of gene therapy due to their lack of specificity of targeting. However, through the introduction of variable antibody domains in a non-conserved loop in the structure of E2, specific populations of cells have been targeted. Furthermore, the use of whole alphaviruses for gene therapy is of limited efficacy both because several internal alphaviral proteins are involved in the induction of apoptosis upon infection and also because the alphaviral capsid mediates only the transient introduction of mRNA into host cells. Neither of these limitations extends to alphaviral envelope pseudotypes of retroviruses or lentiviruses. Various alphavirus-based expression vectors for transgene expression in target cells have been described (Xiong, et al., 1989, Science, 243:1188-91; and Bredenbeek, et al., 1993, J Virol, 67:6439-46). For safety considerations these expression systems usually comprise two plasmids. One plasmid contains the coding sequence of the viral replicon (i.e., nonstructural proteins) and an internal promoter and transgene coding region, while the second plasmid encodes the viral structural genes. These plasmids are used to generate mRNA in vitro, which is then electroporated into host cells to generate one-round infectious virus particles. These viral particles are then used to infect target cells for transgene expression. These particles raise safety concerns, however, because recombination between the sequence elements encoding the non-structural and the structural viral elements can yield replication-competent alphavirus particles having the ability to mediate a significant cytopathic effect in vivo.

A possible solution to this problem is to use unrelated VLPs to deliver alphavirus replicons to the cytoplasm of mammalian cells where they can replicate autonomously and express genes of interest without any nuclear involvement. These VLPs can be produced using three vectors. The first vector comprises the coding sequence for the alphavirus replicon under the control of a mammalian promoter (e.g., CMV), a retroviral-specific RNA packaging signal, and a gene or polynucleotide of interest. The gene may express a protein with therapeutic or research applications, or a shRNA or other regulatory nucleic acid. The second vector comprises retroviral Gag. The third vector would provide the suitable envelope glycoprotein for infection of target cells.

Upon co-transfection into an appropriate packing cell line, RNA molecules transcribed from the cellular promoter present in the first vector will be packaged into VLPs produced from the second vector. These VLPs can deliver the alphavirus-based replicon to a target cell based on the envelope glycoprotein present in the VLPs. Once inside the cell, the host translational machinery will translate the introduced alphavirus RNA and produce alphavirus replication proteins, which will in turn amplify the RNA and express the gene or polynucleotide of interest. Mutant replicons such as the one described above can greatly prolong the duration of expression with minimal impact on the host cell. Moreover, DNA encoding genes for alphavirus structural elements will be absent in the target cell, so the safety of the proposed system is greatly enhanced.

Described herein are compositions relating to VLPs and methods for making and using the described VLPs. The described compositions include VLPs, and vectors and cells used to produce the described VLPs. The related methods described herein relate to methods of producing the VLPs, methods of transducing cells using the VLPs, and methods of producing a protein or polynucleotide of interest in a target cell using the VLPs described herein. Also described are alphavirus-based replicons that allow for expression of proteins or polynucleotides of interest in a target cell without the risk of viral infection.

Described herein are vectors for use in producing VLPs carrying an alphavirus-based replicon that does not encode alphavirus structural proteins. To produce VLPS of this sort, several components may be produced by transfecting or nucleofecting one or more vectors encoding these components into a cell line for in vitro production. In some embodiments, these components are encoded by separate vectors to reduce the likelihood that the resulting VLP will be replication competent. For example, a multi-plasmid system may be used where one plasmid encodes the genetic material, such as an RNA polynucleotide encoding Sindbis virus or VEEV nonstructural proteins, to be packaged by the VLP; another encodes the structural proteins of the VLP, such as gag; and another plasmid encodes a fusion protein, such as VSV-G, to facilitate fusion of the VLP to the membrane of a target cell.

The vectors encoding the genetic material to be packaged by a host cell can take a variety of forms, such as selectable or inducible plasmids, but generally have some common characteristics. For example, vectors encoding an RNA alphavirus-based replicon described herein may include a promoter sequence, a retroviral packaging signal sequence, translation initiation sequences, nonstructural alphavirus proteins, a cloning site for inserting a gene or polynucleotide of interest, an inserted gene or polynucleotide of interest, a 3' untranslated region, and a poly-adenosine tail segment.

In some embodiments the described vectors include a promoter element that allows for segments of the vector to be transcribed by a host cell. In some embodiments the vector sequence may be transcribed into RNA to be packaged into a VLP. In most embodiments of the described vectors, the promoter sequence will be located upstream of all of the translatable elements included within the vector (see for example, FIG. 1 illustrating the location of the cytomegalovirus promoter "pCMV"). In some embodiments described herein the promoter sequence will be derived from a virus, such as CMV, or simian virus 40 (SV40). Numerous other promoter sequences are well known to those skilled in the art and their use with the vectors described herein would be apparent based on the description provided.

In some embodiments the described vectors encoding the genetic material to be packaged by a host cell can include a polynucleotide sequence that encodes a retroviral packaging signal sequence (also known as a psi (T) element) to allow one or two copies of the RNA sequence transcribed from the vector to be packaged into a VLP particle formed in a host cell. Most, if not all, retroviruses have a packaging sequence of this nature, thus these sequences, and their incorporation into the described vectors, will be readily apparent to those skilled in the art. In some embodiments the vectors described herein include a polynucleotide sequence that encodes a retroviral packaging sequence derived from Rous sarcoma virus, Moloney murine leukemia virus, simian immunodeficiency virus (SIV), HIV, human T-lymphotropic virus, and the like. In a particular embodiment, the retroviral packaging sequence is derived from Rous sarcoma virus. Alternatively, the retroviral packaging sequence is derived from murine leukemia virus.

Another aspect of the vectors encoding the genetic material to be packaged by a host cell described herein are translation initiation sequences, which allow the RNA sequence encoded by the vector to be translated in a host cell. In some embodiments the described translation initiation sequences may be capable of allowing for expression of alphavirus-based nonstructural proteins, which can replicate the RNA sequence carried by the described VLPs once it is delivered to the host cell. In some embodiments, the described translation initiation sequences may be capable of allowing for expression of a gene of interest. In some embodiments the translation initiation sequence may allow for the gene of interest to be translated by host cell translation complexes. In some embodiments the translation initiation sequences described herein may be derived from an alphavirus, such as Sindbis virus or VEEV. In other embodiments the translation initiation sequences may be derived from other genes, such as virus genes known to have translation initiation sequences capable of initiating translation of an RNA sequence by mammalian translation complexes. Alternatively, the translation initiation sequences may be derived from other genes, such as the native translation initiation sequence of the gene of interest inserted into the described alphavirus replicon. In some embodiments the translation initiation sequences described herein may be located at more than one location in the packaged RNA molecule, and thus may be encoded one or more times by the described vectors. For example, it may be desirable to translate the described Sindbis or VEEV nonstructural proteins separately from a gene of interest encoded by the package RNA molecule. In such an instance, both the polynucleotide(s) encoding the nonstructural proteins and the polynucleotide encoding the protein of interest will have separate translation initiation sequences located 5' of their position in the vector and packaged RNA. Based on this description, those skilled in the art will understand that a variety of translation initiation sequences capable of promoting the translation of RNA in a mammalian cell may be incorporated to the described VLP-packaged RNAs described herein.

The vectors encoding genetic material to be packaged by a host cell may also include polynucleotides that encode nonstructural alphavirus proteins, such as nonstructural proteins from SIN or VEEV. For example, in some embodiments the described vectors may include polynucleotides that encode one or more Sindbis virus nonstructural proteins. In some embodiments the described vectors may include polynucleotides that encode one or more VEEV nonstructural proteins. In some embodiments described vectors may include polynucleotides that encode the SIN or VEEV nonstructural protein NSP1. In some embodiments described vectors may include polynucleotides that encode the Sindbis virus or VEEV nonstructural protein NSP2. In some embodiments described vectors may include polynucleotides that encode the SIN or VEEV nonstructural protein NSP3. In some embodiments described vectors may include polynucleotides that encode the Sindbis virus or VEEV nonstructural protein NSP4. In some embodiments described vectors may include polynucleotides that encode the SIN or VEEV nonstructural proteins NSP1, NSP2, NSP3, and NSP4. In some embodiments the polynucleotide of the described vector that encodes the alphavirus nonstructural proteins will be derived from the corresponding genomic sequence of an alphavirus genome, such as that of Sindbis virus or VEEV. In some embodiments, the polynucleotides encoding the alphavirus nonstructural proteins are void of any polynucleotides that encode the alphavirus structural proteins, regardless of whether the structural proteins are from the same or a different alphavirus than the nonstructural protein sequences present.

The vector described herein for incorporating genetic material to be packaged by a host cell may also contain a polynucleotide of interest that may be expressed in a host cell transduced by a VLP carrying the genetic material encoded by the vector. In some embodiments the described vectors may encode an RNA polynucleotide sequence to be packaged into a VLP, which can then be delivered to a host cell by VLP-mediated transduction of the cell. Once the RNA polynucleotide sequence has been delivered to the target cell a polynucleotide of interest encoded by the RNA may provide for expression of a protein of interest. Accordingly, the vectors described herein are designed to encode a RNA for packaging into a VLP that can express a gene of interest once inside a target cell. Therefore, in some embodiments the described vectors will include a polynucleotide sequence of interest. In some embodiments of the described vector, the polynucleotide sequence of interest may encode a protein of interest. For example, the polynucleotide sequence of interest may encode green fluorescent protein (GFP) in some embodiments and serve a detectable marker of viral transduction of a target cell. In another embodiment, the polynucleotide sequence of interest may encode a functional version of a protein endogenous to the target cell. In another embodiment, the polynucleotide sequence of interest may encode a functional version of a protein endogenous to the target subject. In another embodiment, the polynucleotide sequence of interest may encode a protein that is foreign to the target cell. In another embodiment, the polynucleotide sequence of interest may encode a protein that is foreign to the target subject. In some embodiments the polynucleotide sequence of interest may encode a protein capable of having a therapeutic effect on a target cell. In some embodiments the polynucleotide sequence of interest may encode a protein capable of having a therapeutic effect on a target subject. In an alternative embodiment the polynucleotide sequence of interest may server as an interfering RNA molecule and function to regulate endogenous gene expression in a host cell. For example, in some embodiments the polynucleotide sequence of interest may comprise a sequence that provides for the formation of an RNA hairpin loop to initiate RNA interference. In addition, the polynucleotide of interest could be a positive or negative sense strand of RNA that can be transcribed by the RNA-dependent RNA polymerase complex formed by the alphavirus nonstructural proteins encoded by the packaged RNA molecule. Since this RNA-dependent RNA polymerase can transcribe RNA in the positive-sense and negative-sense directions, an interfering RNA sequence, such as a miRNA or shRNA, may be inserted into the packaged RNA replicon and can be designed to encode an interfering polynucleotide in either direction. Those of skill in the art will appreciate the therapeutic characteristic of this aspect of the described transduction system, as it can allow for expression of selected proteins in a subject. In accordance with this aspect of the described vector, a cloning site having one or more restriction endonuclease sites may also be included in the vector, to facilitate insertion of a polynucleotide sequence of interest.

Another vector useful in the production of the VLPs described herein is a vector that encodes a virus structural protein. One such class of proteins is the retroviral group-specific antigen (gag) protein. The gag protein is the core structural protein of retroviruses and, in some instances, is capable of forming enveloped virus cores when expressed in eukaryotic cells. This property makes gag proteins particularly useful in the production of VLPs, because they can form the basic structural aspect of the particle and allow for packaging of RNA associated with a retroviral packaging signal sequence. Accordingly, described herein are vectors that include a polynucleotide that encodes a retroviral gag protein. In some embodiments, the described vectors include a polynucleotide that encodes a retroviral gag protein and a promoter polynucleotide sequence that allows for the gag gene sequence to be transcribed into mRNA by host cell RNA polymerase. In one embodiment, the promoter polynucleotide sequence is derived from a virus, such as SV40 or CMV. In some embodiments, the vector will further include a polynucleotide that encodes a protein of interest. Those skilled in the relevant art will understand that a polynucleotide sequence of a gag protein from any retrovirus may be used to produce the vectors and VLPs described herein. In some embodiments the polynucleotide sequence encoding the gag protein may be derived from Rous sarcoma virus. In some embodiments the polynucleotide sequence encoding the gag protein may be derived from murine leukemia virus. In some embodiments the polynucleotide sequence encoding the gag protein may be derived from SIV. In some embodiments the polynucleotide sequence encoding the gag protein may be derived from human T-lymphotropic virus.

Another vector useful in the production of the VLPs described herein is a vector that encodes a protein to mediate fusion between the VLP envelope and a host cell. A class of proteins suitable for this purpose is viral fusion proteins, which facilitate virus infection of cells by allowing an enveloped virus to fuse its membrane with that of a host cell. Many of viral fusion proteins also have known, or suspected, cellular receptor proteins that may allow for targeting of selected cell types, or in cases of more ubiquitous receptors, such as sialic acid for influenza virus, more generalized targeting may be desired. In some instances, viral fusion proteins work in conjunction with viral attachment proteins, ligands for cellular receptor, a receptor for a cell ligand, or accessory proteins, thus proteins of this sort may also be encoded by the described vectors, in addition to, or also by, the vector encoding a viral fusion protein. Alternatively, in some embodiments a viral fusion protein from one virus may be encoded by the described vector along with a viral attachment protein of another virus, a ligand of a cellular receptor, a receptor of a cell ligand, or an accessory protein to facilitate, or direct, targeting of a VLP to a desired cell type. In some embodiments the viral fusion protein, viral attachment protein, ligand of a cellular receptor, receptor of a cell ligand, or accessory protein will be a type-I membrane protein, which will allow the extracellular domain of the protein to be oriented extracellularly when present on the cell surface. This will also allow the fusion protein to be correctly oriented following budding of a VLP from a packaging cell. Expression of such proteins in a cell will typically result in the cell surface being coated with the proteins, so that budding of a VLP from any part of the cell membrane will provide the VLP with some amount of the protein(s) on its surface. In some embodiments, the described vectors include a polynucleotide that encodes a viral fusion protein and a promoter polynucleotide sequence that allows for the fusion protein gene sequence to be translated into mRNA by host cell RNA polymerase. In one embodiment, the promoter polynucleotide sequence is derived from a virus, such as SV40 or CMV. In some embodiments, the described vectors include a polynucleotide that encodes a viral attachment protein and a promoter polynucleotide sequence that allows for the attachment protein gene sequence to be translated into mRNA by host cell RNA polymerase. In one embodiment, the promoter polynucleotide sequence is derived from a virus, such as SV40 or CMV. In some embodiments the vectors described herein include a polynucleotide that encodes a vesicular stomatitis virus G protein. In some embodiments the vectors described herein include a polynucleotide that encodes the influenza hemagglutinin protein. In some embodiments the vectors described herein include a polynucleotide that encodes the influenza neuraminidase protein. In some embodiments the vectors described herein include a polynucleotide that encodes the respiratory syncytial virus fusion protein. In some embodiments the vectors described herein include a polynucleotide that encodes the rotavirus VP7 protein. Other such fusion proteins will be apparent to those skilled in the art based on desired tropism or cell target of the associated virus.

Cells Expressing the Described Vectors

Provided herein are cells comprising the vectors described to produce VLPs. These cells may be used to produce the VLPs described herein by transcribing or expressing the polynucleotides of the vectors. For instance, a mammalian cell transfected with a vector having a polynucleotide sequence encoding an alphavirus RNA construct having a gene or polynucleotide of interest and a packaging signal, a vector encoding a retroviral gag protein, and a vector encoding a viral fusion protein could produce a VLP having the expressed viral fusion protein on its surface with one or two copies of the encoded alphavirus RNA construct housed inside the VLP. Furthermore, because none of these vectors encode alphavirus structural proteins the possibility of creating an infectious virus is substantially reduced compared to systems that do include alphavirus structural proteins.

The described cells may be any eukaryotic cell capable of transcribing, and where necessary (such as in the case of the gag and fusion proteins), translating the polynucleotides of the described vectors. The cells will likely be mammalian cells in many embodiments. For example, rodent cells, such as murine, hamster (CHO or BHK-21), or rat cells could be used to express the described vectors; canine cells, such as Madin Darby canine kidney cells, could be used to express the described vectors; primate cells, such as vero cells, could be used to express the described vectors; and human cells, such as HEK293T cells (human kidney), Hep-2 cells (human airway), Caco-2 (intestine), HeLa (epithelium), and other such cell lines known in the art, could be used to express the described vectors. In some embodiments the described cells can be transfected and selected, using standard transfection and selection methods known in the art, to stably comprise one or more of the described vectors.

In some embodiments the cell lines described herein will contain a vector comprising a polynucleotide sequence encoding an alphavirus replicon wherein the alphavirus replicon encodes a protein of interest, a vector comprising a polynucleotide sequence encoding a gag protein, and a vector comprising a polynucleotide sequence encoding a heterologous fusogenic envelope protein, wherein neither the vectors nor the cell contain a gene encoding an alphavirus structural protein. In some embodiments the alphavirus replicon may be derived from Sindbis virus or VEEV. In some embodiments the alphavirus replicon may have polynucleotide sequences that encode Sindbis virus or VEEV nonstructural proteins NSP1, NSP2, NSP3, NSP4, and a retroviral packaging signal. In some embodiments the retroviral packaging signal may be derived from either Rous sarcoma virus or murine leukemia virus. In some embodiments the polynucleotide sequence encoding the gag protein is derived from Rous sarcoma virus. In some embodiments the polynucleotide sequence encoding the heterologous fusogenic envelope protein encodes VSV-G.

Virus-Like Particles

VLPs produced using the vectors and cells are also described herein. The VLPs described herein will have four general characteristics: they will comprise one or two RNA molecules encoding an alphavirus replicon, and optionally a protein of interest; they will have a viral core comprising a retroviral gag protein, or, in some embodiments, a gag fusion protein; they will have a surface protein to facilitate fusion with a cell, and they will not contain a polynucleotide that encodes an alphavirus structural protein.

The VLPs described herein will be useful in transducing cells in order to express a protein of interest therein. Accordingly, the described VLPs may incorporate one or two alphavirus-based RNA polynucleotides capable of encoding a protein of interest. To facilitate translation of the RNA sequence some embodiments of the described packaged RNA may include translation initiation sequences as described herein. In some embodiments the RNA sequence incorporated into the VLP will include a retroviral packaging sequence that will facilitate inclusion of the RNA into a forming VLP. In some embodiments the retroviral packaging sequence is derived from Rous sarcoma virus, Moloney murine leukemia virus, SIV, HIV, human T-lymphotropic virus, and the like. In a particular embodiment, the retroviral packaging sequence is derived from Rous sarcoma virus. Alternatively, the retroviral packaging sequence may be derived from murine leukemia virus. In addition, the RNA sequences included in the VLP may be capable of encoding nonstructural alphavirus proteins. For example, in some embodiments the packaged RNA may encode one or more Sindbis virus or VEEV nonstructural proteins. In some embodiments the packaged RNA may encode the Sindbis virus or VEEV nonstructural protein NSP1. In some embodiments the packaged RNA may encode the Sindbis virus or VEEV nonstructural protein NSP2. In some embodiments the packaged RNA may encode the Sindbis virus or VEEV nonstructural protein NSP3. In some embodiments the packaged RNA may encode the Sindbis virus or VEEV nonstructural protein NSP4. In some embodiments the packaged RNA may encode the Sindbis virus or VEEV nonstructural proteins NSP1, NSP2, NSP3, and NSP4. The packaged RNA may also include the polynucleotide sequence of a protein of interest. For example, the polynucleotide sequence of interest may encode GFP in some embodiments and serve a detectable marker of viral transduction of a target cell. In another embodiment, the polynucleotide sequence of interest may encode a functional version of a protein endogenous to the target cell. In another embodiment, the polynucleotide sequence of interest may encode a functional version of a protein endogenous to the target subject. In another embodiment, the polynucleotide sequence of interest may encode a protein that is foreign to the target cell. In another embodiment, the polynucleotide sequence of interest may encode a protein that is foreign to the target subject. In some embodiments the polynucleotide sequence of interest may encode a protein capable of having a therapeutic effect on a target cell. In some embodiments the polynucleotide sequence of interest may encode a protein capable of having a therapeutic effect on a target subject. Those of skill in the art will appreciate the therapeutic characteristic of this aspect of the described VLPs, as they can allow for expression of selected proteins in a cell or subject.

The VLPs described herein may also comprise a viral gag protein to provide a viral core structure to the particle. The gag protein is the core structural protein of retroviruses and, in some instances, is capable of forming enveloped virus cores when expressed in eukaryotic cells. This property makes gag proteins particularly useful in the production of VLPs, because they can form the basic structural aspect of the particle and allow for packaging of RNA associated with a retroviral packaging signal sequence. Those skilled in the relevant art will understand that a gag protein from any retrovirus may be used to produce the vectors and VLPs described herein. In some embodiments the gag protein may be derived from Rous sarcoma virus. In some embodiments the gag protein may be derived from murine leukemia virus. In alternative embodiments the gag protein may be derived from SIV, HIV, human T-lymphotropic virus, or similar retrovirus.

Another component of the VLPs described herein is a protein to mediate fusion between the VLP envelope and a host cell. A class of proteins suitable for this purpose is viral fusion proteins, which facilitate virus infection of cells by allowing an enveloped virus to fuse its membrane with that of a host cell. Many of viral fusion proteins also have known, or suspected, cellular receptor proteins that may allow for targeting of selected cell types, or in cases of more ubiquitous receptors, such as sialic acid for influenza virus, more generalized targeting may be achieved. In some instances, viral fusion proteins may work in conjunction with viral attachment proteins, ligands of cellular receptors, receptors of cellular ligands, or accessory proteins, thus proteins of this sort may also be present on the VLP surface in addition to a viral fusion protein. Alternatively, in some embodiments the described VLPs may have a viral fusion protein from one virus and a viral attachment protein of another virus, a ligand of a cellular receptor, a receptor of a cellular ligand, or an accessory protein to facilitate, or direct, targeting of a VLP to a desired cell type. Similarly, the described VLPs may be produced to have more than one fusion protein in the VLP envelope, as this may facilitate fusion to a select variety of cell types. In some embodiments the VLP surface protein(s) will be a type-I membrane protein, which will allow the extracellular domain of the protein to be oriented extracellularly when present on the cell surface. This will also allow the fusion protein to be correctly oriented following budding of a VLP from a packaging cell. Expression of such proteins in a cell will typically result in the cell surface being coated with the proteins, so that budding of a VLP from any part of the cell membrane will provide the VLP with some amount of the fusion protein on its surface. In some embodiments the VLPs described herein include a VSV-G protein to mediate cell fusion. In some embodiments the VLPs described herein include an influenza hemaglutinin protein to mediate cell fusion. In some embodiments the VLPs described herein include an influenza neuraminidase protein to facilitate cell fusion. In some embodiments the VLPs described herein include respiratory syncytial virus fusion protein. In some embodiments the VLPs described herein include the rotavirus VP7 protein. Other such fusion proteins will be apparent to those skilled in the art based on desired tropism or cell target of the associated virus.

The VLPs described herein may comprise an alphavirus replicon, wherein the alphavirus replicon includes a polynucleotide of interest or encodes a protein of interest, retroviral gag protein, and heterologous fusogenic envelope protein; wherein the VLP does not contain an alphavirus structural protein gene. In some embodiments the alphavirus replicon of the VLP is derived from Sindbis virus or VEEV. For example, the VLPs described herein may have an alphavirus replicon encoding Sindbis virus or VEEV non-structural proteins NSP1, NSP2, NSP3, and NSP4. In some embodiments the retroviral packaging signal associated with the packaged RNA in the described VLPs is derived from either Rous sarcoma virus or murine leukemia virus. Based on this description, those skilled in the art will readily understand that the described VLPs may be modified to incorporate aspects of viruses that may facilitate VLP stability, RNA packaging, or cell entry. Such modifications should be understood to be within the scope of the disclosures provided herein.

One embodiment consists of a VLP comprising: an alphavirus replicon comprising a recombinant polynucleotide, wherein the polynucleotide comprises a sequence encoding both subunits of a class II major histocompatibility antigen; a retroviral gag protein, and a fusogenic envelope protein, in which the VLP does not contain an alphavirus structural protein gene.

The recombinant polypeptide of the VLP may further comprise a sequence encoding a costimulatory signal protein. The costimulatory signal protein is preferably selected from the group consisting of CD28, CD80, CD86, and CTLA-4. The costimulatory signal protein most preferably comprises CD80.

Methods of Producing the Described VLPs

The VLPs described herein may be produced in a variety of ways, as will be apparent to those skilled in the art based on the provided disclosure. The commonality to these various methods is the expression of the described vectors in a cell capable of expressing the necessary proteins (gag and a fusion protein) and producing the alphavirus-based RNA replicon. Accordingly, a method of producing a VLP described herein may include co-transforming, transfecting, or nucleofecting a eukaryotic cell with a vector comprising a polynucleotide sequence encoding an alphavirus replicon, wherein the alphavirus replicon includes a polynucleotide of interest or encodes a protein of interest; a vector comprising a polynucleotide sequence encoding a retroviral gag protein; and a vector comprising a polynucleotide sequence encoding a heterologous fusogenic envelope protein; and culturing the co-transformed cell under conditions suitable to cause each vector to produce its encoded product, thereby producing a virus-like particle. In some embodiments the polynucleotide sequence encoding the alphavirus replicon may be derived from Sindbis virus or VEEV. In some embodiments the alphavirus replicon may have polynucleotide sequences that encode Sindbis virus or VEEV nonstructural proteins NSP1, NSP2, NSP3, NSP4, and a retroviral packaging signal. In some embodiments the retroviral packaging signal may be derived from either Rous sarcoma virus or murine leukemia virus. In some embodiments the polynucleotide sequence encoding the gag protein is derived from Rous sarcoma virus. In some embodiments the polynucleotide sequence encoding the heterologous fusogenic envelope protein encodes VSV-G.

Compositions and Methods of Administration

Described herein are compositions comprising at least one described VLP and a pharmaceutically acceptable carrier. Such compositions are useful, for example, for administration to subjects in need of expression of an exogenous protein or increased expression of a protein normally found in those of the same species as the subject. The compositions may be formulated as any of various preparations that are known and suitable in the art, including those described and exemplified herein. In some embodiments, the compositions are aqueous formulations. Aqueous solutions may be prepared by admixing the VLPs in water or suitable physiologic buffer, and optionally adding suitable colorants, flavors, preservatives, stabilizing and thickening agents and the like as desired. Aqueous suspensions may also be made by dispersing the VLPs in water or physiologic buffer with viscous material, such as natural or synthetic gums, resins, methylcellulose, sodium carboxymethylcellulose, and other well-known suspending agents.

The compositions may be formulated for injection into a subject. For injection, the compositions described may be formulated in aqueous solutions such as water or in physiologically compatible buffers such as Hanks's solution, Ringer's solution, or physiological saline buffer. The solution may contain one or more formulatory agents such as suspending, stabilizing or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use. The method described herein may administer the pharmaceutical composition parenterally. The pharmaceutical composition may be administered by intravenous injection. The pharmaceutical composition may be administered by injection within a tissue, preferably a tumor or a cancer.

The compositions may be formulated for aerosolized delivery to a subject. For aerosol delivery, the compositions described may be formulated in aqueous solutions such as water or in physiologically compatible buffers such as Hanks's solution, Ringer's solution, or physiological saline buffer. The solution may contain one or more formulatory agents such as suspending, stabilizing or dispersing agents.

The compositions may be formulated in sustained release vehicles or depot preparations. Such long-acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

Modes of Therapy

The method described herein may be directed to preventing or treating a disease in which the patient has a tumor. The patient may be a cancer patient, preferably a cancer patient is selected from the group of cancer patients having solid tumors derived from breast, cervical, prostate, ovary, renal carcinoma, lung, gastric, pancreas, glioblastoma, and colorectal, most preferably a breast cancer patient. The recombinant polynucleotide accordingly may further comprise a sequence encoding a tumor-specific antigen, preferably a polypeptide selected from the group consisting of alpha fetoprotein (AFP), CA15-3, CA27-29, CA19-9, CA-125, calcitonin, calretinin, carcinoembryonic antigen, chromogranin, cytokeratin, desmin, epithelial membrane protein (EMA), Factor VIII, FL1, glial fibrillary acidic protein (GFAP), gross cystic disease fluid protein (GCDFP-15), HMB-45, human chorionic gonadotropin (hCG), inhibin, keratin, lymphocyte marker, MART-1 (Melan-A), Myo D1, muscle-specific actin (MSA), neurofilament, neuron-specific enolase (NSE), placental alkaline phosphatase (PLAP), prostate-specific antigen, S100 protein, smooth muscle actin (SMA), synaptophysin, thyroglobulin, thyroid transcription factor-1, tumor M2-PK, vimentin, cluster of differention 10 (CD10), CD13, CD15, CD20, CD25, CD30, CD31, CD34, CD45 (PTPRC), CD99, CD117, and a fragment thereof.

The method described herein may administer the pharmaceutical composition parenterally. The pharmaceutical composition may be administered by intravenous injection. The pharmaceutical composition may be administered by injection within the tumor.

In the method described herein the pharmaceutical composition may be administered in combination with a chemotherapeutic drug. The chemotherapeutic drug may be selected from the drug classes consisting of a taxane (paclitaxel or docetaxel), an anthracycline (doxorubicin or epirubicin), cyclophosphamide, capecitabine, tamoxifen, letrozole, carboplatin, gemcitabine, cisplatin, erlotinib, irinotecan, fluorouracil, and oxaliplatin. The pharmaceutical composition may be administered in combination with radiation therapy.

In the method described herein, the pharmaceutical composition induces tumor-specific CD8+ cytolytic T cells. The method further is directed to a pharmaceutical composition comprising the VLP comprising a class II MEW antigen that induces tumor-specific immunity.

The method described herein may be directed to preventing or treating an infectious disease. The recombinant polypeptide accordingly may further comprise a sequence of an infectious agent. The infectious agent may be an infectious virus.

The following examples are provided for illustrative purposes and are meant to enhance, not limit, the preceding disclosure.

Example 1—Production of an Alphavirus-Based Gene Expression System

An alphavirus gene expression system was designed to allow for VLP-mediated delivery an exogenous gene of interest (GOI) or protein of interest (POI) to a target cell with low risk of causing cytopathic viral infection. The expression system was designed using three vectors, which can be expressed in a packaging cell line to produce a transducing VLP. One vector codes for the alphavirus-based expression construct, another vector codes for a retroviral gag protein to facilitate VLP formation, and a third vector codes for a fusion protein to mediate VLP fusion to the host cell. In addition, the system was constructed to work without the need for alphavirus structural proteins being present.

To accomplish this, an alphavirus-based DNA plasmid was produced having a cytomegalovirus promoter (CMV); followed by a retroviral packaging signal of respective retroviral packaging protein GAG; followed by a Sindbis or VEE virus genes encoding nonstructural proteins NSP1, NSP2, NSP3, and NSP4; and finally, one or more subgenomic promoter (SGP; a promoter for virus-encoded RNA-dependent RNA polymerase, resulting in the formation of mRNA) to drive expression of a of a gene of interest (GOI), consisting of a recombinant polynucleotide, and inserted into a multiple cloning site; a 3' untranslated region (URT); and a polyA tail (FIG. 1).

Another plasmid was constructed to encode a retroviral gag protein and a second, optional protein of interest (POI). A third plasmid was constructed to provide expression of a VSV-G viral fusion protein.

Once constructed the plasmids were tested for the ability to produce VLPs carrying a Sindbis virus replicon having a gene of interest. For these experiments, GFP was used as the gene of interest in order to facilitate detection of delivery and intracellular expression of the gene. To produce VLPs, each of the three plasmids described above were transfected into baby hamster kidney (BHK-21) cells using a standard nucleofection procedure with an Amaxa system according to manufacturer instructions (Lonza).

Briefly, the BHK-21 cells at $3\times10^6$ were re-suspended in 100 μl nucleofection solution L (Amaxa) and transferred to tube containing 4.5 μg of plasmid coding for GAG, 3 μg plasmid coding for VSV-G glycoprotein and 100 nanograms of plasmid coding for Sindbis alphavirus replicon or 2.5 micrograms for VEE replicon (in total volume of 10 μl). The mixture of cells and plasmids was transferred to nucleofection cuvette and nucleofected using Amaxa nucleofector II apparatus using settings for BHK-21. The nucleofected cells were re-suspended in 500 μl of completed culture medium and transferred to tissue culture plate containing culture medium solution and incubated at 37° C. for 72-96 hours or for 72 hours at 32° C. After this time supernatants consisting of VLPs and encapsidated alphavirus replicon was clarified by centrifugation at 3000 RPM/10 min at 4° C., filtered by 0.45 um filter and exposed to 10 units of DNAse I (Turbo™-DNAse: Ambion) for 30 min at room temperature. Processed VLPs were stored at 4° C. or frozen on dry ice and transferred to −80° C. As a negative control (fusion-defective VLPs), BHK-21 cells were also nucleofected with only the pCMV-Sin Rep-POI-2 or VEEV-Rep-POI and pGAG-POI-1 plasmids, but not the pEnvelope plasmid encoding VSV-G. Following transfection, the cells were incubated for 48-72 hours in tissue culture medium under normal growth conditions to allow for plasmid-driven production of VLPs. Once the transfected cells were finished incubating, the tissue culture supernatant, which should contain any produced VLPs, was collected. The collected cell supernatants were then added to cultured BHK-21 cells to determine if the cells could be successfully transduced with GFP. Cell supernatants collected from BHK-21 cells transfected with all three plasmids resulted in robust GFP expression when exposed to untransfected BHK-21 cells. Conversely, no GFP expression was observed for untransfected BHK-21 cells incubated with cell supernatants collected from BHK-21 cells transfected with only the pCMV-Sin Rep-POI-2 and pGAG-POI-1 plasmids. Similar experiments were also conducted using human embryonic kidney (HEK293T) cells to demonstrate that the constructed VLPs could transduce human cells. Furthermore, the constructed VLPs can also be stored at 4° C. for at least 30 days without losing the ability to transduce cells.

Experiments were also conducted to assess the ability of VEEV-based alpha virus replicon to express protein in cells. For these studies BHK-21 cells were transduced with VLPs having a *Gaussia* luciferase gene inserted into a VEEV replicon. Following transduction, cell supernatants monitored for expression of luciferase protein. High amounts of luciferase were detected in the supernatants of cells transduced with the VEEV replicon having the *Gaussia* luciferase gene, relative to control VEEV replicons without an exogenous gene, or with a gene encoding GFP. Additionally, expression of the luciferase protein increased rapidly after transduction. Similar results were also observed in the context of delivering functional cre recombinase (red cells) to cells engineered to express GFP in the absence of cre recombinase.

Cells were transduced in parallel with either Sindbis-based VLPs encoding GFP or VEEV-based VLPs encoding GFP. Both alphavirus-based VLPs caused robust GFP expression, while the cells transduced with VEEV-based VLPs were observed to have the higher expression levels.

Example 2—Expression of Multiple Proteins in Target Cells Transduced with VEE VLPs The basic concept of RNA delivery using VLP is shown in FIG. 2. In this experiment, a breast cancer model was used. A double promoter vector of the replicon was developed for expressing HLA-DR1 and CD80 (FIG. 3). A VLP encoding these two antigens was used to infect 4T1-Luc2 breast cancer cells. Using anti-HLA-DR and CD80 antibodies, the results showed that both proteins are indeed express in this cell. HLA-DR1 and CD80 are expressed in 4T1-Luc2 cells transfected with a VLP with the VLP-VEE replicon of FIG. 2. HLA-DR1 expressing cells were identified by a FITC-labeled, anti-HLA-DR antibody. CD80 expressing cells were identified by a PE-labeled, anti-CD80 antibody.

To assess whether an alphavirus replicon can express two separate proteins in the same cell, experiments were performed using a VEE replicon having HLA-DR1 under the control of one subgenomic promoter and CD80 under a another subgenomic promoter. Following production of VLPs having the described VEE replicon, cells were transduced and examined for expression of both proteins. As shown in FIG. 4, transduced cells were able to express both proteins (immunolabeled HLA-DR1 is shown in green (FITC) and CD80 shown in red (phycoerythrin).

Example 3—Expression of Multiple Proteins in Target Cells Transduced with VEE VLPs To test the VLP in a mouse animal system. 4T1-Luc2 cells, highly aggressive and metastatic breast cancer cells, were implanted into the mammary fat pad of ten mice. Tumors were visible within a few days and were apparent and palpable (5-7 mm) within a week. Three of the mice were injected intratumorally with a VLP expressing an inert protein (GFP), two mice were injected with a VLP expressing human HLA-DR1/CD80 (xenogeneic), and five mice remained non-injected as a control.

After one week, tumors were surgically removed from all mice and tumor regrowth and metastasis were followed over several weeks. The results (FIG. 5) showed that 4 out of 5 non-injected mice (untreated controls) died within 4-6 weeks due to cancer regrowth and metastasis in lung, breast and liver. All three VLP/GFP (non-specific protein controls) injected mice were also died within 4-6 weeks due to cancer regrowth and metastasis in lung, breast and liver. However, both VLP/HLA-DR1/CD80 treated mice remained alive for more than 25 weeks with no sign of tumor development.

Figure 5:
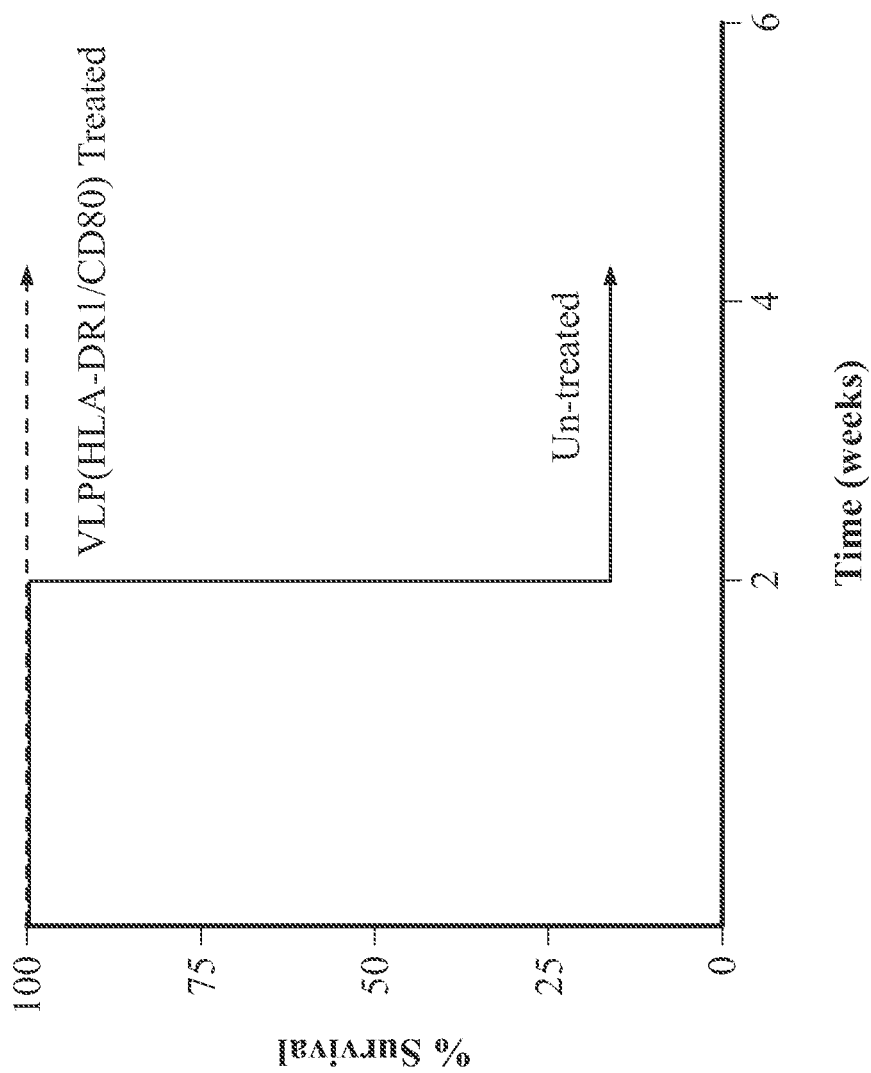
FIG. 5 shows immunized animal survival after challenge with 4T1-Luc2 cells.

In order to show that mice indeed developed immunity against the tumor cells, the mice that survived the previous experiment were challenged again with 4T1-Luc2 cells. Four new controls mice were also included. In the challenge experiment, all mice were intravenously injected with 10,000 4T1-Luc2 cells and tumor growth and progression were monitored. If the mice developed immunity, the mice that survived will not develop a tumor and no metastasis will be found. If there is no immunity, the mice will succumb to metastatic cancer. Four control animals succumbed to metastatic cancer within two weeks of intravenous injection of 4T1-Luc2 cells, whereas the animals treated with therapeutic VLPs survived after more than 4 weeks of challenge (FIG. 5). This is indicative that the HLA/CD80 treated animals have acquired immunity against tumor cells.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

TABLE 1

SEQ ID NO: 1

```
   1 gacggatcgg gagatctccc gatcccctat
     ggtgcactct cagtacaatc tgctctgatg 61 ccgcatagtt aagccagtat ctgctccctg
     cttgtgtgtt ggaggtcgct gagtagtgcg 121 cgagcaaaat ttaagctaca acaaggcaag
     gcttgaccga caattgcatg aagaatctgc 181 ttagggttag gcgttttgcg ctgcttcgcg
     atgtacgggc cagatatacg cgttgacatt 241 gattattgac tagttattaa tagtaatcaa
     ttacggggtc attagttcat agcccatata 301 tggagttccg cgttacataa cttacggtaa
     atggcccgcc tggctgaccg cccaacgacc 361 cccgcccatt gacgtcaata atgacgtatg
     ttcccatagt aacgccaata gggactttcc 421 attgacgtca atgggtggag tatttacggt
     aaactgccca cttggcagta catcaagtgt 481 atcatatgcc aagtacgccc cctattgacg
     tcaatgacgg taaatggccc gcctggcatt 541 atgcccagta catgacctta tgggactttc
     ctacttggca gtacatctac gtattagtca 601 tcgctattac catggtgatg ccgttttggc
     agtacatcaa tgggcgtgga tagcggtttg 661 actcacgggg atttccaagt ctccaccccca
     ttgacgtcaa tgggagtttg ttttggcacc 721 aaaatcaacg ggactttcca aaatgtcgta
     acaactccgc cccattgacg caaatgggcg 781 gtaggcgtgt acggtgggag gtctatataa
     gcagagctcg tatggacata ttgtcgttag 841 aacgcggcta caattaatac ataaccttat
     gtatcataca catacgattt aggggacact 901 atagattgac ggcgtagtac acactattga
     atcaaacagc cgaccaattg cactaccatc 961 acaatggaga agccagtagt aaacgtagac
     gtagaccccc agagtccgtt tgtcgtgcaa 1021 ctgcaaaaaa gcttcccgca atttgaggta
     gtagcacagc aggtcactcc aaatgaccat 1081 gctaatgcca gagcattttc gcatctggcc
     agtaaactaa tcgagctgga ggttcctacc 1141 acagcgacga tcttggacat aggcagcgca
     ccggctcgta gaatgttttc cgagcaccag 1201 tatcattgtg tctgcccat gcgtagtcca
     gaagacccgg accgcatgat gaaatacgcc 1261 agtaaactgg cggaaaaagc gtgcaagatt
     acaaacaaga acttgcatga gaagattaag 1321 gatctccgga ccgtacttga tacgccggat
     gctgaaacac catcgctctg ctttcacaac 1381 gatgttacct gcaacatgcg tgccgaatat
     tccgtcatgc aggacgtgta tatcaacgct
```

TABLE 1-continued

SEQ ID NO: 1

```
1441 cccggaacta tctatcatca ggctatgaaa
     ggcgtgcgga ccctgtactg gattggcttc 1501 gacaccaccc agttcatgtt ctcggctatg
     gcaggttcgt accctgcgta caacaccaac 1561 tcggccgacg agaaagtcct tgaagcgcgt
     aacatcggac tttgcagcac aaagctgagt 1621 gaaggtagga caggaaaatt gtcgataatg
     aggaagaagg agttgaagcc cgggtcgcgg 1681 gtttatttct ccgtaggatc gacactttat
     ccagaacaca gagccagctt gcagagctgg 1741 catcttccat cggtgttcca cttgaatgga
     aagcagtcgt acacttgccg ctgtgataca 1801 gtggtgagtt gcgaaggcta cgtagtgaag
     aaaatcacca tcagtcccgg gatcacggga 1861 gaaaccgtgg gatacgcggt tacacacaat
     agcgagggct tcttgctatg caaagttact 1921 gacacagtaa aaggagaacg ggtatcgttc
     cctgtgtgca cgtacatccc ggccaccata 1981 tgcgatcaga tgactggtat aatggccacg
     gatatatcac ctgacgatgc acaaaaactt 2041 ctggttgggc tcaaccagcg aattgtcatt
     aacggtagga ctaacaggaa caccaacacc 2101 atgcaaaatt accttctgcc gatcatagca
     caagggttca gcaaatgggc taaggagcgc 2161 aaggatgatc ttgataacga gaaaatgctg
     ggtactgagag aacgcaagct tacgtatggc 2221 tgcttgtggg cgtttcgcac taagaaagta
     cattcgtttt atcgcccacc tggaacgcag 2281 acctgcgtaa aagtcccagc ctctttagc
     gcttttccca tgtcgtccgt atggacgacc 2341 tctttgccca tgtcgctgag gcagaaattg
     aaactggcat tccaaccaaa gaaggaggaa 2401 aaactgctgc aggtctcgga ggaattagtc
     atggaggcca aggctgcttt tgaggatgct 2461 caggaggaag ccagagcgga gaagctccga
     gaagcacttc caccattagt ggcagacaaa 2521 ggcatcgagg cagccgcaga agttgtctgc
     gaagtggagg ggctccaggc ggacatcgga 2581 gcagcattag ttgaaacccc gcgcggtcac
     gtaaggataa tacctcaagc aaatgaccgt 2641 atgatcggac agtatatcgt tgtctcgcca
     aactctgtgc tgaagaatgc caaactcgca 2701 ccagcgcacc cgctagcaga tcaggttaag
     atcataacac actccggaag atcaggaagg 2761 tacgcggtcg aaccatacga cgctaaagta
     ctgatgccag caggaggtgc cgtaccatgg 2821 ccagaattcc tagcactgag tgagagcgcc
     acgttagtgt acaacgaaag agagtttgtg 2881 aaccgcaaac tataccacat tcccatgcat
     ggccccgcca agaatacaga agaggagcag 2941 tacaaggtta caaaggcaga gcttgcagaa
     acagagtacg tctttgacgt ggacaagaag 3001 cgttgcgtta agaaggaaga agcctcaggt
     ctggtcctct cgggagaact gaccaaccct 3061 ccctatcatg agctagctct ggagggactg
     aagacccgac ctgcggtccc gtacaaggtc 3121 gaaacaatag gagtgatagg cacaccgggg
     tcgggcaagt cagctattat caagtcaact 3181 gtcacggcac gagatcttgt taccagcgga
     aagaaagaaa attgtcgcga aattgaggcc 3241 gacgtgctaa gactgagggg tatgcagatt
     acgtcgaaga cagtagattc ggttatgctc 3301 aacgatgcc acaaagccgt agaagtgctg
     tacgttgacg aagcgttcgc gtgccacgca 3361 ggagcactac ttgccttgat tgctatcgtc
     aggccccgca gaaggtagt actatgcgga 3421 gaccccatgc aatgcggatt cttcaacatg
     atgcaactaa aggtacattt caatcaccct 3481 gaaaagaca tatgcaccaa gacattctac
     aagtatatct cccggcgttg cacacagcca 3541 gttacagcta ttgtatcgac actgcattac
     gatgaaaga tgaaaaccac gaacccgtgc 3601 aagaagaaca ttgaaaatcga tattacaggg
     gccacaaagc cgaagccagg ggatatcatc 3661 ctgacatgtt tccgcgggtg ggttaagcaa
     ttgcaaatcg actatcccgg acatgaagta 3721 atgacagccg cggcctcaca agggctaacc
     agaaaaggag tgtatgccgt ccggcaaaaa 3781 gtcaatgaaa acccactgta cgcgatcaca
     tcagagcatg tgaacgtgtt gctcacccgc 3841 actgaggaca ggctagtgtg gaaaaccttg
     cagggcgacc catggattaa gcagcccact 3901 aacatacta aaggaaactt tcaggctact
     atagaggact gggaagctga acacaaggga 3961 ataattgctg caataaacag ccccactccc
     cgtgccaatc cgttcagctg caagaccaac 4021 gtttgctggg cgaaagcatt ggaaccgata
     ctagccacgg ccggtatcgt acttaccggt 4081 tgccagtgga gcgaactgtt cccacagttt
     gcggatgaca aaccacattc ggccatttac 4141 gccttagacg taatttgcat taagtttttc
     ggcatggact tgacaagcgg actgtttcct 4201 aaacagagca tcccactaac gtaccatccc
     gccgattcag cgaggccggt agctcattgg 4261 gacaacagcc caggaacccg caagtatggg
     tacgatcacg ccattccgc cgaactctcc 4321 cgtagatttc cggtgttcca gctagctggg
     aagggcacac aacttgattt gcagacgggg 4381 agaaccagag ttatctctgc acagcataac
     ctggtcccgg tgaaccgcaa tcttcctcac 4441 gccttagtcc ccgagtacaa ggagaagcaa
     cccggcccgg tcaaaaaatt cttgaaccag 4501 ttcaaacacc actcagtact tgtggtatca
     gaggaaaaaa ttgaagctcc ccgtaagaga
```

TABLE 1-continued

SEQ ID NO: 1

```
4561 atcgaatgga tcgccccgat tggcatagcc
     ggtgcagata agaactacaa cctggctttc 4621 gggtttccgc cgcaggcacg gtacgacctg
     gtgttcatca acattggaac taaatacaga 4681 aaccaccact ttcagcagtg cgaagaccat
     gcggcgacct taaaaaccct ttcgcgttcg 4741 gccctgaatt gccttaaccc aggaggcacc
     ctcgtggtga agtcctatgg ctacgccgac 4801 cgcaacagtg aggacgtagt caccgctctt
     gccagaaagt ttgtcagggt gtctgcagcg 4861 agaccagatt gtgtctcaag caatacagaa
     atgtacctga ttttccgaca actagacaac 4921 agccgtacac ggcaattcac cccgcaccat
     ctgaattgcg tgatttcgtc cgtgtatgag 4981 ggtacaagag atggagttgg agccgcgccg
     tcataccgca ccaaaaggga gaatattgct 5041 gactgtcaag aggaagcagt tgtcaacgca
     gccaatccgc tgggtagacc aggcgaagga 5101 gtctgccgtg ccatctataa acgttggccg
     accagtttta ccgattcagc cacggagaca 5161 ggcaccgcaa gaatgactgt gtgcctagga
     aagaaagtga tccacgcggt cggccctgat 5221 ttccggaagc acccagaagc agaagccttg
     aaaattgctac aaaacgccta ccatgcagtg 5281 gcagacttag taaatgaaca taacatcaag
     tctgtcgcca ttccactgct atctacaggc 5341 atttacgcag ccggaaaaga ccgccttgaa
     gtatcactta actgcttgac aaccgcgcta 5401 gacagaactg acgcggacgt aaccatctat
     tgcctggata agaagtggaa ggaaagaatc 5461 gacgcggcac tccaacttaa ggagtctgta
     acagagctga aggatgaaga tatggagatc 5521 gacgatgagt tagtatggat tcatccagac
     agttgcttga agggaagaaa gggattcagt 5581 actacaaaag gaaaattgta ttcgtacttc
     gaaggcacca aattccatca agcagcaaaa 5641 gacatggcgg agataaaggt cctgttccct
     aatgaccagg aaagtaatga acaactgtgt 5701 gcctacatat tgggtgagac catggaagca
     atccgcgaaa agtgcccggt cgaccataac 5761 ccgtcgtcta gcccgcccaa aacgttgccg
     tgcctttgca tgtatgccat gacgccagaa 5821 agggtccaca gacttagaag caataacgtc
     aaagaagtta cagtatgctc ctccaccccc 5881 cttcctaagc acaaaattaa gaatgttcag
     aaggttcagt gcacgaaagt agtcctgttt 5941 aatccgcaca ctccgcatt cgttcccgcc
     cgtaagtaca tagaagtgcc agaacagcct 6001 accgctcctc ctgcacaggc cgaggaggcc
     cccgaagttg tagcgcacacc gtcaccatct 6061 acagctgata acacctcgct tgatgtcaca
     gacatctcac tggatatgga tgacagtagc
```

```
6121 gaaggctcac tttttcgag ctttagcgga
     tcggacaact ctattactag tatggacagt 6181 tggtcgtcag gacctagttc actagagata
     gtagaccgaa ggcaggtggt ggtggctgac 6241 gttcatgccg tccaagagcc tgcccctatt
     ccaccgccaa ggctaagaa gatggcccgc 6301 ctggcagcgg caagaaaaga gcccactcca
     ccggcaagca atagctctga gtccctccac 6361 ctctcttttg tgggtatc catgtccctc
     ggatcaattt tcgacggaga gacggcccgc 6421 caggcagcgg tacaaccct ggcaacaggc
     cccacgatg tgcctatgtc tttcggatcg 6481 ttttccgacg gagagattga tgagctgagc
     cgcagagtaa ctgagtccga acccgtcctg 6541 tttggatcat ttgaaccggg cgaagtgaac
     tcaattatat cgtcccgatc agccgtatct 6601 tttccactac gcaagcagag acgtagacgc
     aggagcagga ggactgaata ctgactaacc 6661 ggggtaggtg ggtacatatt ttcgacggac
     acaggccctg ggcacttgca aaagaagtcc 6721 gttctgcaga accagcttac agaaccgacc
     ttggagcgca atgtcctgga aagaattcat 6781 gccccggtgc tcgacacgtc gaaagaggaa
     caactcaaac tcaggtacca gatgatgccc 6841 accgaagcca acaaaagtag gtaccagtct
     cgtaaagtag aaaatcagaa agccataacc 6901 actgagcgac tactgtcagg actacgactg
     tataactctg ccacagatca gccagaatgc 6961 tataagatca cctatccgaa accattgtac
     tccagtagcg taccggcgaa ctactccgat 7021 ccacagttcg ctgtagctgt ctgtaacaac
     tatctgcatg agaactatcc gacagtagca 7081 tcttatcaga ttactgacga gtacgatgct
     tacttggata tggtagacgg gacagtcgcc 7141 tgcctggata ctgcaacctt ctgccccgct
     aagcttagaa gttacccgaa aaaacatgag 7201 tatagagccc cgaatatccg cagtgcggtt
     ccatcagcga tgcagaacac gctacaaaat 7261 gtgctcattg ccgcaactaa aagaaattgc
     aacgtcacgc agatgcgtga actgccaaca 7321 ctggactcag cgacattcaa tgtcgaatgc
     tttcgaaaat atgcatgtaa tgacgagtat 7381 tgggaggagt tcgctcggaa gccaattagg
     attaccactg agtttgtcac cgcatatgta 7441 gctagactga aaggccctaa ggccgccgca
     ctatttgcaa agacgtataa tttggtccca 7501 ttgcaagaag tgcctatgga tagattcgtc
     atggacatga aaagagacgt gaaagttaca 7561 ccaggcacga aacacacaga agaaagaccg
     aaagtacaag tgtacaaagc cgcagaaccc 7621 ctggcgactg cttacttatg cgggattcac
     cgggaattag tgcgtaggct tacggccgtc
```

TABLE 1-continued

SEQ ID NO: 1

```
 7681 ttgcttccaa acattcacac gcttttcgac
      atgtcggcgg aggattttga tgcaatcata 7741 gcagaacact tcaagcaagg cgacccggta
      ctggagacgg atatcgcatc attcgacaaa 7801 agccaagacg acgctatggc gttaaccggt
      ctgatgatct tggaggacct gggtgtggat 7861 caaccactac tcgacttgat cgagtgcgcc
      tttggagaaa tatcatccac ccatctacct 7921 acgggtactc gtttaaatt cggggcgatg
      atgaaatccg gaatgttcct cacacttttt 7981 gtcaacacag ttttgaatgt cgttatcgcc
      agcagagtac tagaagagcg gcttaaaacg 8041 tccagatgtg cagcgttcat tggcgacgac
      aacatcatac atggagtagt atctgacaaa 8101 gaaatggctg agaggtgcgc cacctggctc
      aacatggagg ttaagatcat cgacgcagtc 8161 atcggtgaga gaccaccttta cttctgcggc
      ggatttatct tgcaagattc ggttacttcc 8221 acagcgtgcc gcgtggcgga tccctgaaa
      aggctgttta agttgggtaa accgctccca 8281 gccgacgacg agcaagacga agacagaaga
      cgcgctctgc tagatgaaac aaaggcgtgg 8341 tttagagtag gtataacagg cactttagca
      gtggccgtga cgacccggta tgaggtagac 8401 aatattacac ctgtcctact ggcattgaga
      acttttgccc agagcaaaag agcattccaa 8461 gccatcagag gggaaataaa gcatctctac
      ggtggtccta aatagtcagc atagtacatt 8521 tcatctgact aatactacaa caccaccacc
      tctagagctt gccgccacca tggtgagcaa 8581 gggcgaggag ctgttcaccg gggtggtgcc
      catcctgtc gagctggacg gcgacgtgaa 8641 cggccacaag ttcagcgtgt ccggcgaggg
      cgagggcgat gccacctacg gcaagctgac 8701 cctgaagttc atctgcacca ccggcaagct
      gcccgtgcc tggcccaccc tcgtgaccac 8761 cctgacctac ggcgtgcagt gcttcagccg
      ctaccccgac cacatgaagc agcacgactt 8821 cttcaagtcc gccatgcccg aaggctacgt
      ccaggagcgc accatcttct tcaaggacga 8881 cggcaactac aagacccgcg ccgaggtgaa
      gttcgagggc gacacccctgg tgaaccgcat 8941 cgagctgaag ggcatcgact tcaaggagga
      cggcaacatc ctggggcaca gctggagta 9001 caactacaac agccacaacg tctatatcat
      ggccgacaag cagaagaacg gcatcaaggt 9061 gaacttcaag atccgccaca acatcgagga
      cggcagcgtg cagctcgccg accactacca 9121 gcagaacacc cccatcggcg acggcccgt
      gctgctgccc gacaaccact acctgagcac 9181 ccagtccgcc ctgagcaaag accccaacga
      gaagcgcgat cacatggtcc tgctggagtt
```

```
 9241 cgtgaccgcc gccgggatca ctcacggcat
      ggacgagctg tacaagtaaa gcggccgtga 9301 gcatgcaggc cttgggccca atgatccgac
      cagcaaaact cgatgtactt ccgaggaact 9361 gatgtgcata atgcatcagg ctggtacatt
      agatccccgc ttaccgcggg caatatagca 9421 acactaaaaa ctcgatgtac ttccgaggaa
      gcgcagtgca taatgctgcg cagtgttgcc 9481 acataaccac tatattaacc atttatctag
      cggacgccaa aaactcaatg tatttctgag 9541 gaagcgtggt gcataatgcc acgcagcgtc
      tgcataactt ttattatttc ttttattaat 9601 caacaaaatt ttgtttttaa catttcaaaa
      aaaaaaaaaa aaaaaaaaaa aaaaaaaaa 9661 aaagggaatt cctcgattaa ttaagcggcc
      gctcgagatg gcacacgtgt tacggtttta 9721 ccgtcgacct ctagctagag cttggcgtaa
      tcatggtcat agctgtttcc tgtgtgaaat 9781 tgttatccgc tcacaattcc acacaacata
      cgagccggaa gcataaagtg taaagcctgg 9841 ggtgcctaat gagtgagcta actcacatta
      attgcgttgc gctcactgcc cgctttccag 9901 tcgggaaacc tgtcgtgcca gctgcattaa
      tgaatcggcc aacgcgcggg gagaggcggt 9961 ttgcgtattg ggcgctcttc cgcttcctcg
      ctcactgact cgctgcgctc ggtcgttcgg 10021 ctgcggcgag cggtatcagc tcactcaaag
      gcggtaatac ggttatccac agaatcaggg 10081 gataacgcag gaaagaacat gtgagcaaaa
      ggccagcaaa aggccaggaa ccgtaaaaag 10141 gccgcgttgc tggcgttttt ccataggctc
      cgcccccctg acgagcatca caaaaatcga 10201 cgctcaagtc agaggtggcg aaacccgaca
      ggactataaa gataccaggc gtttccccct 10261 ggaagctccc tcgtgcgctc tcctgttccg
      accctgccgc ttaccggata cctgtccgcc 10321 tttctccctt cgggaagcgt ggcgctttct
      catagctcac gctgtaggta tctcagttcg 10381 gtgtaggtcg ttcgctccaa gctgggctgt
      gtgcacgaac cccccgttca gcccgaccgc 10441 tgcgccttat ccggtaacta tcgtcttgag
      tccaacccgg taagacacga cttatcgcca 10501 ctggcagcag ccactggtaa caggattagc
      agagcgaggt atgtaggcgg tgctacagag 10561 ttcttgaagt ggtggcctaa ctacggctac
      actagaagaa cagtatttgg tatctgcgct 10621 ctgctgaagc cagttacctt cggaaaaaga
      gttggtagct cttgatccgg caaacaaacc 10681 accgctggta gcggtggttt ttttgtttgc
      aagcagcaga ttacgcgcag aaaaaaagga 10741 tctcaagaag atcctttgat cttttctacg
      gggtctgacg ctcagtggaa cgaaaactca
```

TABLE 1-continued

SEQ ID NO: 1

```
10801 cgttaaggga ttttggtcat gagattatca
      aaaaggatct tcacctagat cctttaaat 10861 taaaaatgaa gttttaaatc aatctaaagt
      atatatgagt aaacttggtc tgacagttac 10921 caatgcttaa tcagtgaggc acctatctca
      gcgatctgtc tatttcgttc atccatagtt 10981 gcctgactcc ccgtcgtgta gataactacg
      atacgggagg gcttaccatc tggcccagt 11041 gctgcaatga taccgcgaga cccacgctca
      ccggctccag atttatcagc aataaaccag 11101 ccagccgaa gggccgagcg cagaagtggt
      cctgcaactt tatccgcctc catccagtct 11161 attaattgtt gccgggaagc tagagtaagt
      agttcgccag ttaatagttt gcgcaacgtt 11221 gttgccattg ctacaggcat cgtggtgtca
      cgctcgtcgt ttggtatggc ttcattcagc 11281 tccggttccc aacgatcaag gcgagttaca
      tgatccccca tgttgtgcaa aaaagcggtt
```

SEQ ID NO: 1

```
11341 agctccttcg gtcctccgat cgttgtcaga
      agtaagttgg ccgcagtgtt atcactcatg 11401 gttatggcag cactgcataa ttctcttact
      gtcatgccat ccgtaagatg cttttctgtg 11461 actggtgagt actcaaccaa gtcattctga
      gaatagtgta tgcggcgacc gagttgctct 11521 tgcccggcgt caatacggga taataccgcg
      ccacatagca gaactttaaa agtgctcatc 11581 attggaaaac gttcttcggg gcgaaaactc
      tcaaggatct taccgctgtt gagatccagt 11641 tcgatgtaac ccactcgtgc acccaactga
      tcttcagcat cttttacttt caccagcgtt 11701 tctgggtgag caaaaacagg aaggcaaaat
      gccgcaaaaa agggaataag ggcgacacgg 11761 aaatgttgaa tactcatact cttcctttt
      caatattatt gaagcattta tcagggttat 11821 tgtctcatga gcggatacat atttgaatgt
      atttagaaaa ataaacaaat aggggttccg 11881 cgcacatttc cccgaaaagt gccacctgac
      gtc
```

What is claimed:

1. A method of treating a tumor in a mammalian subject comprising administering to the subject a pharmaceutical composition comprising a virus like particle (VLP), the VLP comprising:
 a. an alphavirus replicon comprising a recombinant polynucleotide, wherein the polynucleotide comprises:
  (i) a sequence encoding both subunits of a human class II major histocompatibility (MHC) antigen, and
  (ii) a sequence encoding a costimulatory signal protein selected from the group consisting of CD80, CD28, CD86, and CTLA-4;
 b. a retroviral gag protein, and
 c. a fusogenic envelope protein,
wherein the VLP does not contain an alphavirus structural protein gene, wherein the VLP is not cytopathic to a eukaryotic cell and wherein the VLP is administered to the mammalian subject by in vivo parenteral, subcutaneous, or intravenous administration, or administration directly into a tumor.

2. The method according to claim 1, wherein the costimulatory signal protein comprises CD80.

3. The method according to claim 2, wherein the human class II major histocompatibility (MHC) antigen comprises HLA-DR1.

4. The method according to claim 1, wherein the alphavirus replicon comprises nucleic acid sequence of Sindbis virus or Venezuelan equine encephalitis virus.

5. The method according to claim 1, wherein the alphavirus replicon further comprises a sequence encoding Sindbis virus or Venezuelan equine encephalitis virus nonstructural proteins NSP1, NSP2, NSP3, and NSP4; and a retroviral packaging signal derived from Rous sarcoma virus.

6. The method according to claim 1, wherein the VLP does not comprise or express a retroviral pol gene.

7. The method according to claim 1, wherein the retroviral gag protein is a Rous sarcoma virus gag protein.

8. The method according to claim 1, wherein the fusogenic envelope protein is a glycoprotein.

9. The method according to claim 1, wherein the fusogenic envelope protein binds specifically to a tumor cell.

10. The method according to claim 1, wherein the alphavirus replicon comprises a subgenomic promoter operably linked to HLA-DR1 and another subgenomic promoter operably linked to CD80.

11. The method according to claim 1, wherein said treating or preventing comprises inducing tumor-specific immunity.

12. The method according to claim 1, wherein the mammalian subject is a cancer patient selected from the group of cancer patients having solid tumors derived selected from breast, cervical, prostate, ovary, renal carcinoma, lung, gastric, pancreas, glioblastoma, and colorectal tumors.

13. The method according to claim 1, wherein the pharmaceutical composition is administered in combination therapy with a chemotherapeutic drug.

14. The method according to claim 13, wherein the chemotherapeutic drug is selected from the group consisting of a taxane, an anthracycline, cyclophosphamide, capecitabine, tamoxifen, letrozole, carboplatin, gemcitabine, cisplatin, erlotinib, irinotecan, fluorouracil, and oxaliplatin.

15. The method according to claim 1, wherein the pharmaceutical composition is administered in combination therapy with radiation therapy.

* * * * *

UNITED STATES PATENT AND TRADEMARK OFFICE
CERTIFICATE OF CORRECTION

| | |
|---|---|
| PATENT NO. | : 12,049,639 B2 |
| APPLICATION NO. | : 18/174013 |
| DATED | : July 30, 2024 |
| INVENTOR(S) | : Deb K. Chatterjee and Stanislaw J. Kaczmarczyk |

Page 1 of 1

It is certified that error appears in the above-identified patent and that said Letters Patent is hereby corrected as shown below:

In the Claims

In Column 34, Claim 12, Line 29, please delete "cancer patients having solid tumors derived selected from" and insert -- cancer patients having solid tumors selected from --

Signed and Sealed this
Twelfth Day of August, 2025

Coke Morgan Stewart
*Acting Director of the United States Patent and Trademark Office*